United States Patent [19]

McGinity et al.

[11] Patent Number: 5,288,502

[45] Date of Patent: Feb. 22, 1994

[54] PREPARATION AND USES OF MULTI-PHASE MICROSPHERES

[75] Inventors: James W. McGinity, Austin, Tex.; Motokazu Iwata, Osaka, Japan

[73] Assignee: The University of Texas System, Austin, Tex.

[21] Appl. No.: 779,173

[22] Filed: Oct. 16, 1991

[51] Int. Cl.⁵ .......................... A61K 9/14; B32B 5/16
[52] U.S. Cl. ................................... 424/484; 424/488; 424/489; 424/490; 424/491; 428/402.2; 428/402.21; 428/402.22
[58] Field of Search ............... 424/489, 490, 491, 488, 424/484; 428/402.2, 402.21, 402.22

[56] References Cited

U.S. PATENT DOCUMENTS

| | | | |
|---|---|---|---|
| 3,565,559 | 2/1971 | Sato et al. | 424/491 |
| 4,652,441 | 3/1987 | Okada et al. | |
| 4,954,298 | 9/1990 | Yamamoto et al. | |
| 5,049,322 | 9/1991 | Devissoguet et al. | 424/490 |

OTHER PUBLICATIONS

Alex et al. (1987) N. J. Microencapsulation, vol. 7, No. 3, 347-355 Encapsulation of Water Soluble Drugs by a Modified Solvent Evaporation Method. In: Effect of Process and Formulation Variable on Drug Entrapment.

Cohen, et al., (1990), N. Pharmaceutical Research 8(6): 713-720, Controlled Delivery Systems for Proteins Based on Poly(Lactic/Glycolic Acid) Microspheres.

Patent Cooperation Treaty International Search Report, Mar. 17, 1993.

Primary Examiner—Paul R. Michl
Assistant Examiner—Peter F. Kulkosky
Attorney, Agent, or Firm—Arnold, White & Durkee

[57] ABSTRACT

Multi-phase polymeric microspheres containing a molecular compound dispersed in a polymeric matrix are described. Methods for preparing the multi-phase microspheres are also described, which includes a multiple emulsion solvent evaporation technique. Drug loading efficiencies between 80 to 100% were achieved using the described methods. Particular ratios of the W/O emulsion to polymer, and concentration of surfactant and dispersion media (mineral oil) provide highly efficient multi-phase microspheres. In particular embodiments, the multi-phase microspheres feature a high loading efficiency of water-soluble drugs, and also eliminates partitioning of the water soluble agent into the polymer acetonitrile (solvent) phase, thus preventing low encapsulation efficiency. The described multiphase microspheres possess efficient drug loading, release properties, and drug stability, and also provide a vehicle for long term therapeutic release of a biologically active molecule for therapeutically effective periods of time. Molecular compounds which may be incorporated within the multi-phase microspheres include both water-soluble and water-insoluble drugs, proteins (e.g. TNF), peptides, and chemicals. The molecular compound is protected within an oily droplet, and contact with polymer, surfactant, organic solvents, and other potentially denaturing agents is prevented.

62 Claims, 16 Drawing Sheets

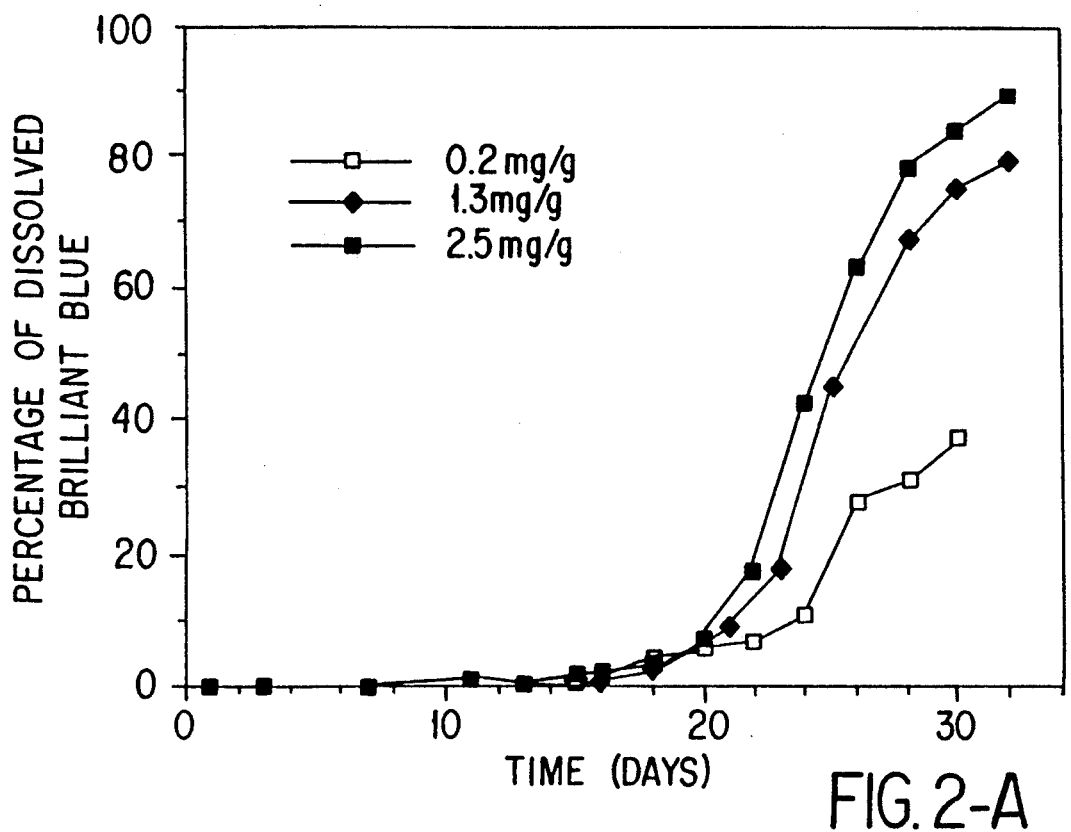
FIG. 2-A
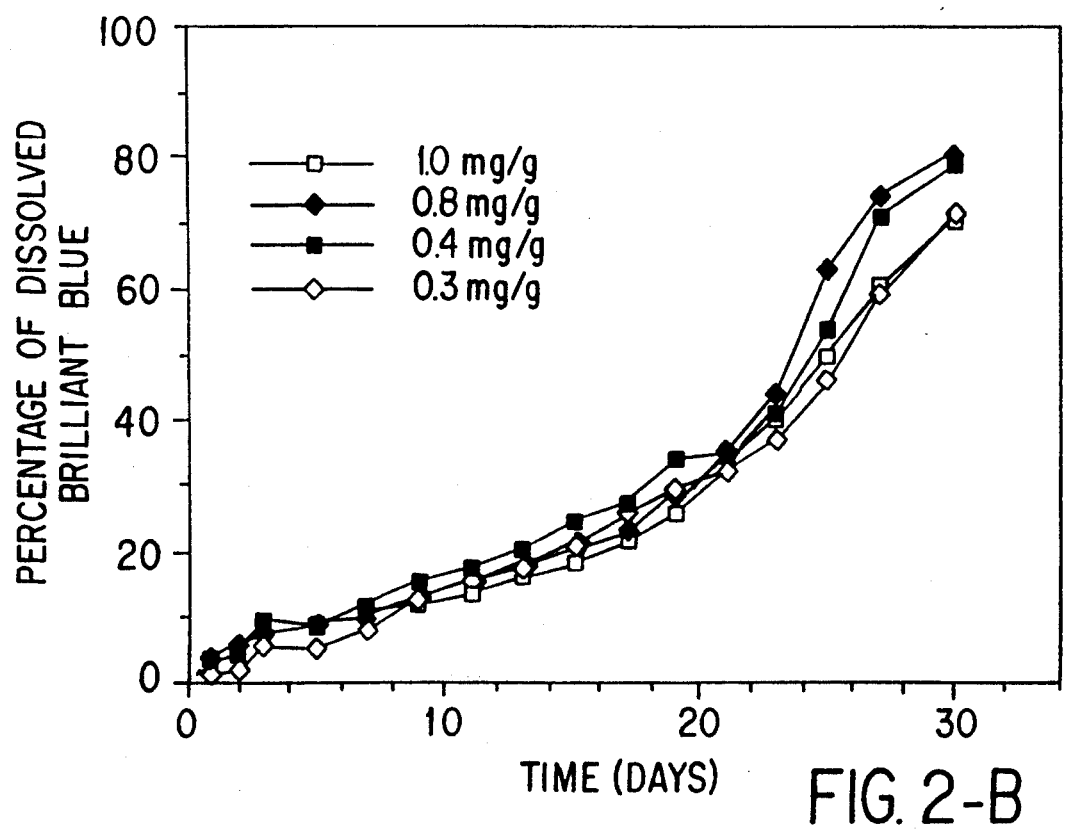
FIG. 2-B

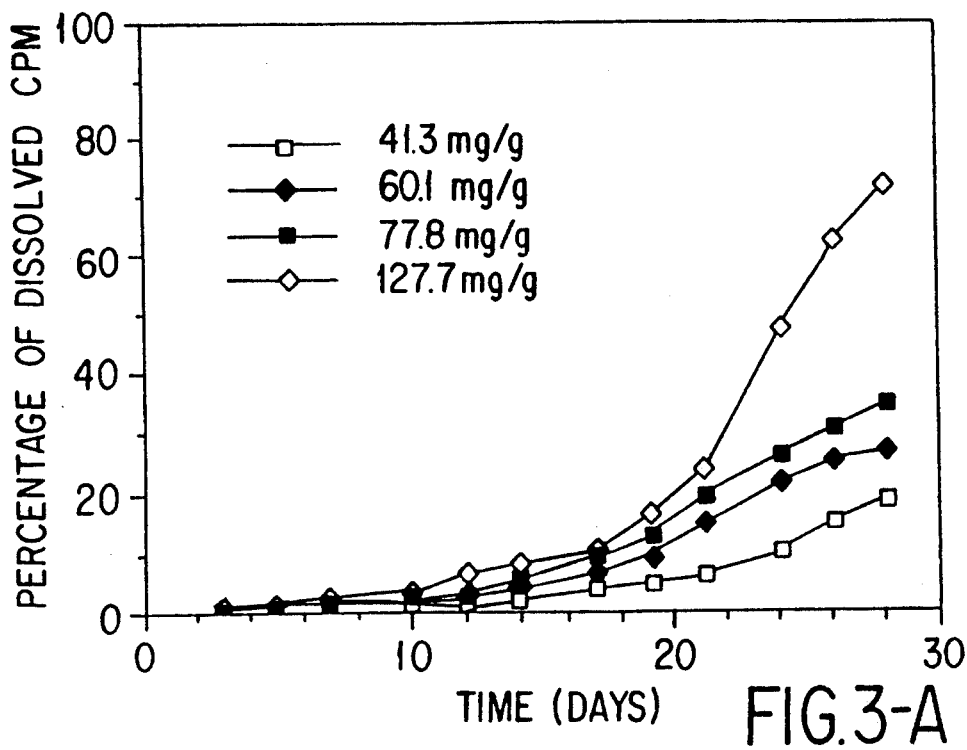
FIG. 3-A
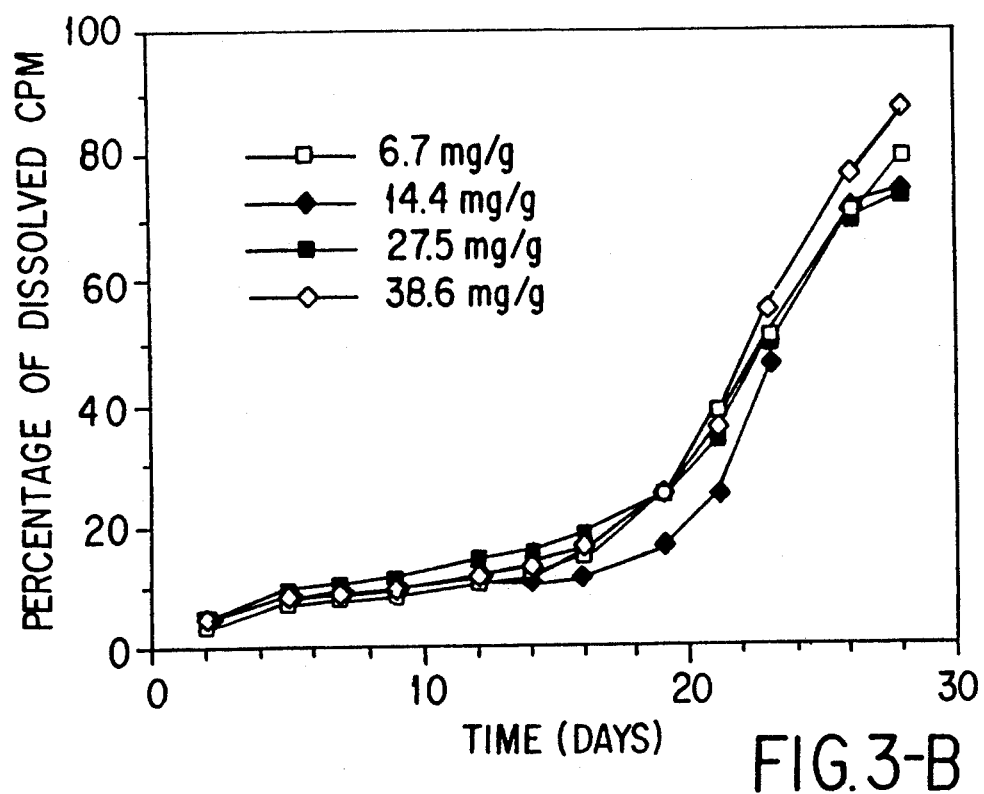
FIG. 3-B

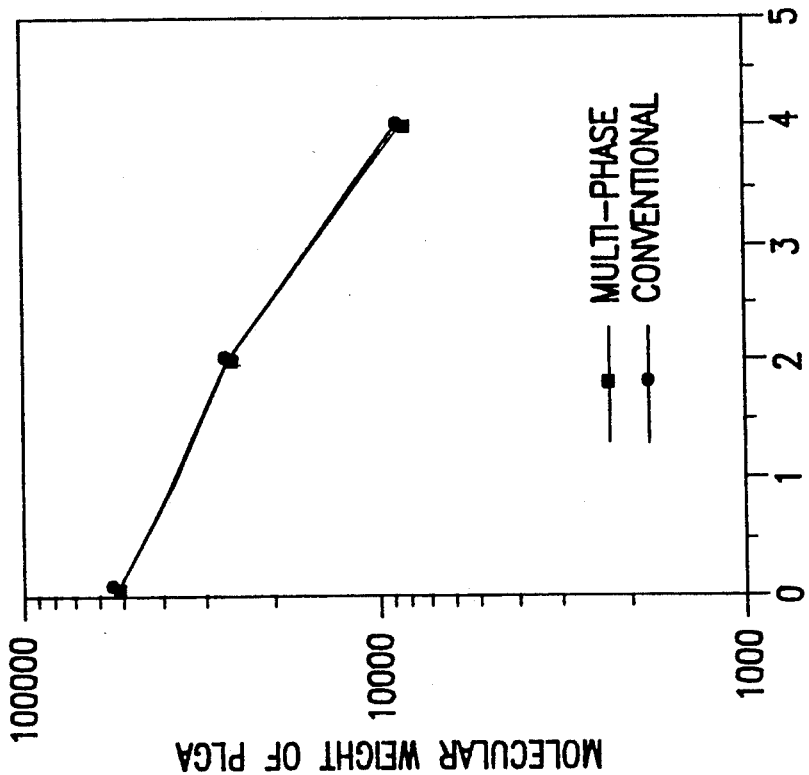
FIG.10-B
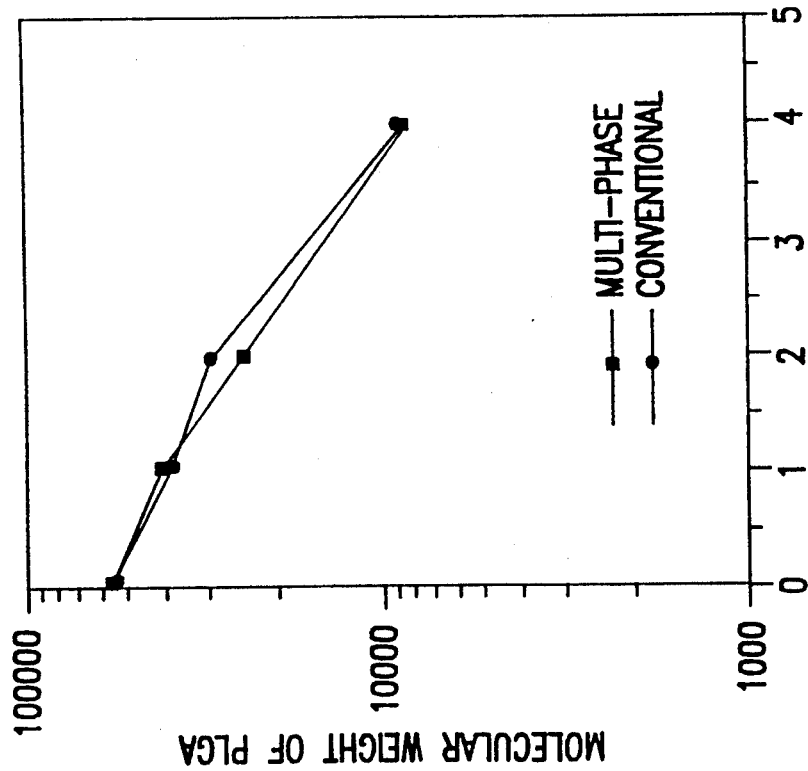
FIG.10-A

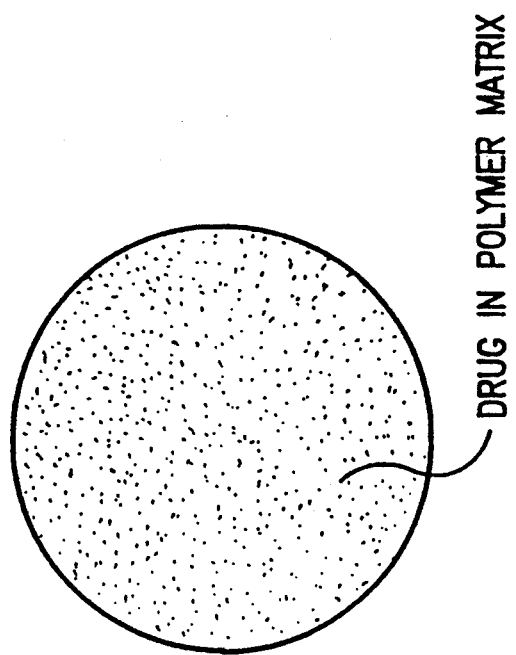
FIG.11-B
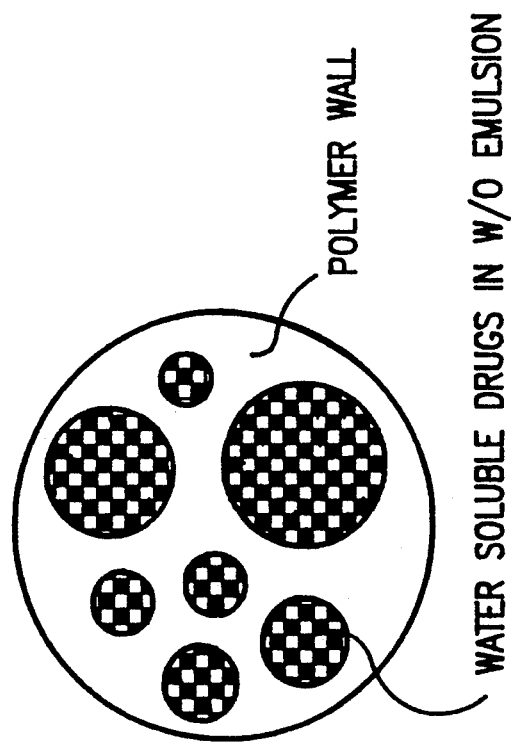
FIG.11-A

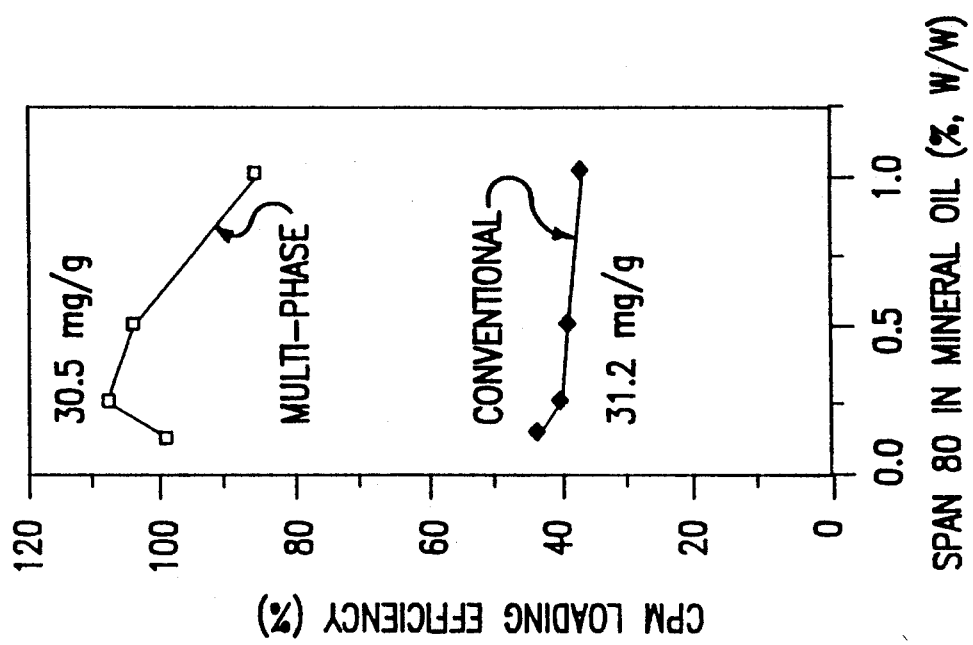
FIG.14-B
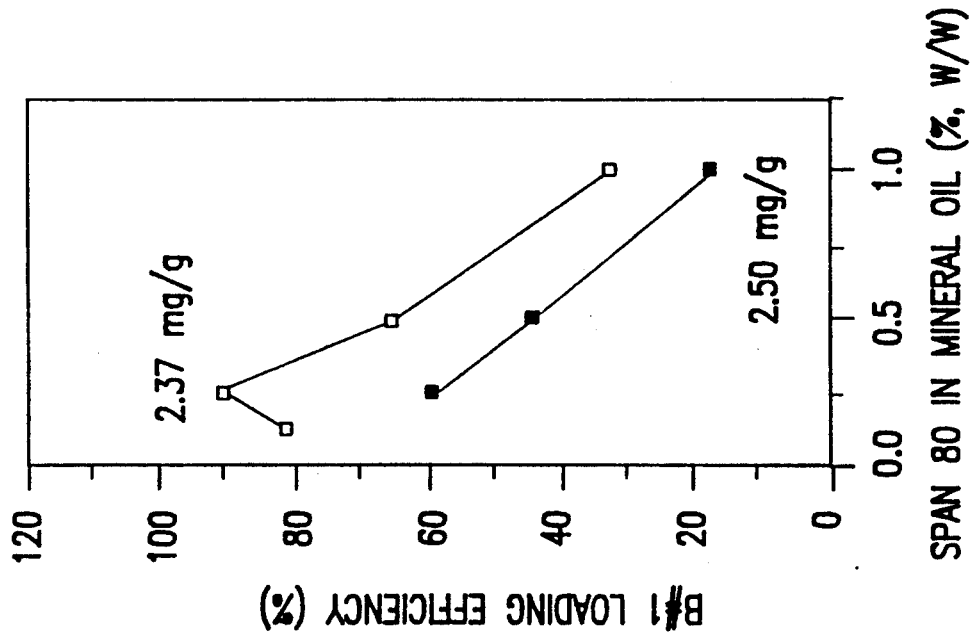
FIG.14-A

PREPARATION AND USES OF MULTI-PHASE MICROSPHERES

BACKGROUND OF THE INVENTION

1. Field of the Invention

The present invention relates to the field of drug delivery systems, particularly those which involve microcapsules or microspheres. In addition, the present invention proposes methods for the preparation of particular multi-phase microspheres, as well as methods for their use in treating animals, including humans. The presently described microspheres also relate generally to the field of biodegradable in vivo delivery devices for proteins, peptides and other molecular compounds.

2. Background of the Art

The preparation and synthesis of a number of recombinant proteins has been the subject of a recent upsurge in research efforts. However, many proteins and peptides have short biological half lives, and as a consequence, delivery of most therapeutically valuable pharmaceuticals requires a regimen of multiple individual injections for desired therapeutic efficacy in a patient.

one way in which multiple individual injection regimens have been avoided is through the use of biodegradable microcapsules, preferably those which are capable of releasing the particular biologically active molecule continuously and at a controlled rate. Most preferably and ideally, such a system would provide for a continuous and controlled rate of drug delivery over a therapeutically valuable period of time. Such methods for the delivery of therapeutically valuable substances, such as proteins, peptides and pharmacologically active molecules, as well as systems for their effective delivery in an animal, have become important areas of research. However, for so-me biologically active molecules, a therapeutically effective delivery period will require continuous and sustained delivery over weeks or even months. In this regard, encapsulated pharmaceuticals have achieved only limited success, with days/weeks being the limit of even the most protracted systems available.

Present delivery systems include biodegradable microspheres and/or microcapsules which include biodegradable polymers, such poly d,l-lactic acid (PLA) and copolymers of tactic acid and glycolic acid (PLGA). These particular polymers are currently the most widely used biodegradable polymers employed in sustained release devices. Copolymers of tactic acid and glycolic acid may be obtained by polycondensation of lactic acid or glycolic acid in the presence[34] or in the absence[35] of a catalyst or other activator. Microcapsules prepared from such materials may be administered intramuscularly or by other parenteral routes.

Some PLA and PLGA microspheres exist which contain water-soluble compounds such as quinidine sulfate[1,2], luteinizing hormone releasing hormone (LHRH) agonist[5,6], and less water-soluble drugs such as phenobarbitone[3,4]. Biodegradable microspheres have also been reported which contain such drugs as steroids[11,13], anticancer agents[12,14], cardiac drugs[15], and peptides[6,16,17], specifically prepared with the polymers polylactic acid and copolymers of lactic acid and glycolic acid. The biological response modifiers (BRMS) have also been described in association with particular microcapsules.

However, the water solubility of a number of biologically active molecular compounds has proven to be one of the most limiting factors in optimizing molecular compound loading efficiency in biodegradable microspheres and/or microcapsules, specifically, when a conventional oil/water emulsion system is used in the solvent evaporation process. In this regard, it has been observed that the loading efficiency of water-soluble drugs into, for example, PLA or PLGA-polymeric microspheres is relatively low when conventional oil/water systems are used in a solvent evaporation process[1,31]. This has been attributed to the observation that such drugs readily diffuse into the aqueous outer phase of the emulsion system.

Some of the inventors' prior work[1] addresses the low efficiency of drug loading due to solubility problems by adjusting the pH of the aqueous phase in the microencapsulation procedure. Adjusting the pH of the aqueous phase was shown to maximize loading efficiency of the particular water-soluble molecule, quinidine sulfate, in PLA microspheres, using a conventional O/W emulsion system in the solvent evaporation process. One of the inventors had found that by increasing the pH of the water soluble molecular compound solution, the solubility of the water soluble molecular compound will increase in the solution. Thus, the water soluble molecular compound is prevented/inhibited from diffusing from the microcapsule into the external aqueous phase.

Anhydrous emulsion systems have also been described in the preparation of microcapsules. For example, a phenobarbitone microencapsulation system was developed by Jalil and Nixon (1989)[18] using poly(1-lactic acid). Acetonitrile was used as the solvent ("W"-phase) for the poly(1-lactic acid) and the drug, and light mineral oil was used as the continuous dispersion medium (O-phase). However, in these microspheres, drug particles were dispersed in direct contact with the polymer matrix (conventional "matrix-type" system).

Direct contact of drug particles with a polymer matrix has been observed to contribute to degradation of a protein,[7] perhaps by monomer and diner residues present in the polymer (inventors' unpublished observations). Polymeric degradation would also result in such "matrix" systems upon incorporation of proteins or enzymes in such a system, as direct contact with the polymer is again not prevented.

Most of the microspheres described in the literature belong to the class of "matrix-type" drug delivery capsules, in which the "foreign" (i.e. drug) particles are dispersed homogeneously in direct contact with the polymer. These processes also frequently involve direct contact between the drug and a polymer solvent, such as acetonitrile or methylene chloride. In these systems, direct contact between the particular biologically active molecule and the polymer, the polymer solvent or with enzymes in the biological system promote degradation of the intended pharmaceutical. Specifically, previous workers have shown that the monomer and dimer residues in the polymer may degrade the protein, and other workers have shown that proteins[7,32] and enzymes[33] in direct contact with the polymer will result in polymeric degradation over time.

In order to avoid interactions of sensitive substances (i.e., protein/peptides) with particular polymers, such as PLA and PLGA, in a delivery system, multiple-walled microcapsular devices employing conventional multiple emulsion techniques were proposed. For example, emulsion techniques have been reported using polymers to form microspheres having a multiple walled structure. For example, albumin containing-biodegradable microspheres have been reported by Saha et al.[25] using an O/W/O multiple emulsion solvent evaporation technique. In addition, Morris et al.[24] described a three-ply walled microsphere composed of acacia/ethylcellulose/acacia layers prepared by using a W/O/W multiple emulsion solvent evaporation technique. However, drug loading capacities of these devices are limited in that sufficient amounts of the polymer must be present to facilitate formation of a stable microsphere. While the use of highly potent drugs may circumvent the drug-loading capacity problem, sufficiently "controlled" biodegradable systems for providing a constant and controlled drug release to justify the high cost of potent drug proteins and peptides are not currently available.

Despite the advantages to be gained from a multi-walled microsphere delivery device, the systems thus far described are limited to relatively low levels of drug loading capacity, since sufficient polymer must be present in order to form a sufficiently stable -microsphere. Carefully controlled drug release and high efficiency in drug loading (preferably more than 90%) are required features in clinically efficacious microencapsulation techniques, particularly in light of the high potency and in many cases, prohibitive costs of synthetic peptide/-protein drugs.

Drug loading capacity loading efficiency, stability and controlled releases have been observed as limiting factors even when highly potent water soluble drugs are incorporated into microparticles. Thus, difficulties relating to the accomplishment of carefully controlled and sufficiently extended drug release rates remain. In addition, potential drug degradation from direct contact of the particular biologically active molecule and the polymer as well as from contact of the polymer with enzymes in vivo, potentially remain.

Present techniques used by biotechnology and pharmaceutical companies to encapsulate peptides in biodegradable polymers utilize a solvent-nonsolvent system which unfortunately suffers from the disadvantage of high solvent residuals, poor content uniformity of the peptide in the microspheres, and instability due to the contact of the biological agent with the polymer, organic solvent (e.g. methylene chloride, acetonitrile), and some cases, a surfactant.

Thus, while some biotechnology companies in the United States, Japan and Europe have achieved some measure of success in developing potent peptides and proteins for a variety of clinical conditions, major challenges remain to be solved by pharmaceutical scientists in developing stable and optimized control-release formulations for potent water soluble bioactive agents. Thus, a microcapsule delivery system which permitted the efficient loading of water-soluble biologically active molecules in a biodegradable carrier system would provide a medically significant advance in the clinically valuable and cost-effective preparations for long-term in vivo drug delivery of potent water-soluble chemicals, proteins and peptides.

SUMMARY OF THE INVENTION

The present invention provides a unique multi-phase microsphere system having a high drug loading efficiency, and, methods for preparing same, which feature a drug/protein contained within a fixed oil to efficiently incorporate virtually any molecular compound. The method for preparing the multi-phase microspheres which contain a water-soluble molecular compound, for example, is generally described for purposes of the present invention as a multiple emulsion solvent evaporation technique. In a most preferred aspect of the present invention, a multi-phase microsphere system for the efficient incorporation of a water soluble molecular compound is provided. Molecular compounds which are not water soluble may also be employed in the presently described multi-phase microspheres. Such molecular compounds may be prepared together in a fixed oil directly, with the resulting mixture then being added to a polymer and solvent solution and a "dispersion" oil medium, so as to provide multi-phase microsphere.

Molecular compounds which are not stable in an aqueous solution may also be employed with the described multi-phase microspheres. For molecular compounds which are not particularly stable in water (e.g., subject to denaturation), the multi-phase microspheres of the present invention may be prepared by drying the final microspheres under a vacuum to remove any water which may be present in the microemulsion of the multi-phase microsphere.

For molecular compounds which may become unstable from dehydration, and where the stability of the molecular compound is sensitive to water, the described delivery system may be provided by suspending an amount of the molecular compound directly in a fixed oil, such as soybean oil, which may then be combined with a polymer and polymer solvent solution in a "dispersion" medium, such as mineral oil (where the polymer solvent is acetonitrile In all of the delivery systems described, the molecular compound is protected against continued denaturation from any included water. Alternatively, the microemulsion of the multi-phase microspheres of the present invention, containing a molecular compound which is unstable in water, may be prepared by first lyophilizing a preparation of the molecular compound in water and oil. The lyophilization will act to remove or decrease the water content of the preparation, thus preserving the stability of the molecular compound. The lyophilized form of the preparation thus takes on a powder form which may then be emulsified in a solution of a polymer and polymer solvent in a "dispersion" oil medium.

For purposes of describing the subject matter of the present invention, the term, "multi-phase" relates to a modified matrix type microsphere wherein the molecular compound is not in direct contact with the polymer, while the term "conventional" relates to a matrix type of microsphere structure wherein the drug is dissolved or dispersed throughout the polymer matrix the drug being in direct contact with the polymer.

An "emulsion" for purposes of describing the present invention is a stable dispersion of one liquid in a second immiscible liquid.[29] An example of such would be milk. An "immiscible" liquid is a liquid which is not soluble in another substance or liquid, for example, oil in water.[30] In contrast, two substances that are mutually soluble in all proportions are is. said to be miscible.[30]

In one particularly preferred aspect of the present invention, a microemulsion of a fixed oil and an aqueous solution of a water-soluble molecular compound, such as a protein, peptide or other water-soluble chemical if prepared. This emulsion is of the "water-in-oil" type (oil as the continuous phase) as opposed to an "oil-in-water" system (water as the continuous phase). The term "continuous phase" as used in the description of the present invention is the external phase, as compared to the "dispersed phase", which is the internal phase.

The protein, peptide, chemical or other drug either after lyophilization of the molecular compound in a fixed oil mixture (in the case of a protein, peptide or drug denatured in the presence of water) or as a microemulsion prepared from the molecular compound in an aqueous phase in water (in the case of a protein, peptide or drug which is not denatured in the presence of water), is incorporated as part of the multi-phase microsphere of the present invention. The "external" oil phase of the microsphere includes an oil, such as mineral oil, which is incompatible with the particular solvent of a polymer-insolvent preparation.

As the molecular compound of the present invention is effectively "trapped" within multiple tiny oil droplet reservoirs throughout the polymer matrix, the incorporated molecular compound does not partition into the polymer-insolvent outer phase during formulation, or into the polymer matrix of the hardened solvent evaporated multi-phase microsphere. Aluminum monostearate also helps to increase the viscosity of the fixed oil in which the molecular compound is effectively held, thus further preventing the molecular compound from diffusing out of the microsphere.

A multiple emulsion technique with organic solvents to form microcapsules has been described generally in the past. However, none of the prior reported systems describe or suggest either a system wherein a water-insoluble molecular compound in a fixed oil, or a microemulsion of an aqueous solution of a water soluble protein or drug in a fixed oil, is prepared and subsequently formulated in combination with a polymer-insolvent solution and dispersion (oil) medium. The present inventors describe for the first time molecular compound-in-oil preparation (mixture or microemulsion) as part of a multi-phase microsphere system. This unique design prevents contact of the molecular compound with potentially degrading substances, such as the polymer. The novel approach of lyophilizing a microemulsion of a particular water-denatured or unstable molecular compound and water in a fixed oil and mixing the lyophilized product with a solution of polymer and solvent in a dispersion oil broadens the applicability of the present invention for use with virtually any compound.

The basic technological breakthrough provided with the present disclosure may be applied in preparing slow-release, long-acting, multi-phase microspheres with virtually any micro- or macromolecule, including synthetic, potent proteins and peptides. Thus, the proposed compositions and methods present a highly cost effective and therapeutically valuable delivery system.

In one particular embodiment of the present invention, a delivery system for a molecular compound comprising a multi-phase microsphere which includes a molecular compound contained within a fixed oil as part of a polymeric matrix is provided. The term "molecular compound" as used in the description of the present invention includes peptides, proteins as well as other biocompatible and/or potentially bioactive/pharmacologically active molecules. Potentially useful molecular compounds which may be formulated in the disclosed multi-phase microspheres of the present invention include a variety of compounds known as "drugs" and other biocompatible macro- and micromolecules.

Those compounds which are substantially or only partially soluble in water may also be used in conjunction with the disclosed multi-phase microsphere system upon enhancing the water solubility of the particular compound through adjustment of pH of the agent/compound in a water solution etc. before preparation of the aqueous solution of the water soluble agent/compound in oil to form a "microemulsion". Alternatively, molecular compounds which are unstable or exhibit minimal stability due to dehydration or denaturation upon exposure to water may be formulated as described with an additional step being included wherein the final multi-phase microspheres are dried under vacuum to remove any water from the microspheres. A second option of preparing a water/oil microemulsion of the drug and oil, as already described, with the microemulsion being lyophilized to remove or decrease the water content exists to preserve stability. Such a system would result in finely dispersed particles in the oil phase prior to the encapsulation process. The lyophilized powder which results may then be emulsified in a polymer and solvent and a dispersion oil medium.

By way of example, molecular compounds which may be used in conjunction with the present invention included tumor-necrosis factor (TNF-$\alpha$ and $\beta$), chlorpheniramine maleate (CPM), diphenhydramine hydrochloride (DPH), promazine hydrochloride (PMZ), and procainamide hydrochloride (PRC). Other pharmacologically active substances which may be prepared as a "microemulsion" of the present system, upon slight adjustment of pH, include the interferons (IFN-$\alpha$, $\beta$, $\gamma$) macrophage activating factor (MAF), the interleukins (IL-1,2,3,4,5,6), colony stimulating factor (CSF), tumor degenerating factor (TDF), epidermal growth factor (EGF), erythropoietin (EPO), tissue plasminogen activator (TPA), insulin, urokinase, luteinizing hormone releasing hormone (LHRH), monoclonal antibodies, superoxide dismutase (SOD), the P-450 enzymes, bovine serum albumin (BSA), and oxytocin. Other water soluble molecular compounds which may be used in conjunction with the described method for preparing multi-phase microspheres include the steroids and atriopeptin III.

Most preferably, those water-soluble molecular compounds most preferred for use in the presently disclosed multi-phase microspheres are chlorpheniramine maleate (CPM), diphenhydramine hydrochloride (DPH), procainamide hydrochloride, promazine hydrochloride (PMZ), or brilliant blue.

Most preferably, the multi-phase microspheres of the present invention are about 150 microns ($\mu$) in size. Even more preferably, the microspheres are between 50$\mu$ and 100$\mu$ in size. However, the microspheres of the present invention may be formulated to achieve virtually any size less than 150$\mu$ by adjustment of agitation rates, viscosity of the emulsion (i.e., lowering the viscosity of the oil), increasing the temperature used during formulation etc., sufficient to decrease particle size and prevent separation of the "microemulsion" particles from the polymer-insolvent mixture during formulation.

The multi-phase microspheres of the present invention further include a polymeric substance. The polymers poly (d,l-lactic acid) and poly (d,l-lactic) co-glycolic tactic acid are included as among the most preferred polymers to be used in conjunction with the presently disclosed multi-phase microspheres. However, virtually any biodegradable and biocompatible polymer may be used in the preparation of the present invention. The biocompatible polymer must be soluble in a solvent which is immiscible with the dispersion medium of choice (for example, the dispersion medium mineral oil).

The microemulsions (i.e., drug/protein solution-in-oil emulsion) described as part of the inventive multi-phase microspheres may be prepared with any variety of fixed oils. By way of example, such fixed oils include safflower, soybean, peanut, cotton seed, sesame, or cod liver oil. Soybean, sesame, and safflower oil are most preferred in the preparation of the described "microemulsion". Oils used clinically in intravenous fat emulsions include the soybean and safflower oils.

Mineral oil is most preferably used as part of the "dispersion" medium in the invention. The microemulsion, lyophilized molecular compound product or anhydrous molecular compound in fixed oil preparation is combined with a polymer/solvent in such a mineral oil dispersion medium to form the multiple emulsion of the invention. However, any oil may be used in the "dispersion" medium which is incompatible with the particular solvent used to dissolve the polymer.

The present inventors have found that, provided the protein is stable in water, the formation of a microemulsion of the aqueous water-soluble protein molecular compound solution in oil, will stabilize the protein by preventing contact of the protein molecule directly with the polymer, the organic solvents, if any used, and any surfactants used to prepare the microspheres. Thus, the delivery system of the present invention includes an aqueous molecular compound solution-in-oil emulsion of the water soluble molecular compound which comprises numerous tiny oily reservoirs within the polymer matrix of the multi-phase microsphere. The water-soluble molecular compound thereby remains essentially isolated from all potentially degrading substances.

The multi-phase microspheres of the delivery system comprise water soluble molecular compounds such as water-soluble proteins, peptides or drugs. Most preferably, the water-soluble molecular compound of the described delivery system includes CPM. In a most particularly preferred embodiment of the described delivery system, the molecular compound tumor-necrosis factor in water is prepared in the fixed oil, soybean oil, and the mixture lyophilized to a powder. The microemulsion of TNF in water with oil is lyophilized to remove essentially all of the water before dispersion of the microemulsion in the polymer solution (polymer plus polymer solvent), the mixture of which is then combined in a "dispersion" oil.

The present disclosure demonstrates a number of important differences between the present inventive multi-phase microspheres and other microsphere and microcapsule systems. Specifically, while particular polymer degradation rates between the two types of microspheres (i.e., multi-phase V. conventional) were almost the same, the drug dissolution rate from the microsphere in each of the systems was significantly different. Specifically, the molecular compound dissolution rates of the conventional microspheres were demonstrated to increase as the overall drug content of the microsphere was increased. In contrast, the multi-phase microspheres disclosed herein were demonstrated to release the particular compounds incorporated therein at a rate independent of the particular molecular compound content of the microsphere.

This important observation highlights one particular advantage of the present systems over those proposed in the literature, in that a constant and fixed rate of delivery of a molecular compound is provided without sacrificing high drug loading efficiency in the microsphere. Other systems must be modified in order to achieve any particular rate of drug delivery, and currently do not provide for extended and slow drug release over therapeutically useful periods of time. The constant and slow rate of drug delivery may be attributable to the design of the multi-phase microspheres, which require that the molecular compound first traverse the water-oil barrier, and the polymer barrier of the polymer matrix, before the molecular compound/drug may diffuse out of the microsphere into the surrounding media or system (e.g., the system of an animal). Highly controlled and constant drug release is accomplished, along with the added advantage of greater than 80% drug loading efficiencies of these agents.

Another aspect of the present invention includes a method for providing sustained release of a molecular compound (most preferably, water soluble molecular compounds) in an animal. One particularly preferred embodiment of this method comprises preparing a formulation comprising polymeric multi-phase microspheres containing a microemulsion of the water soluble molecular compound in a fixed oil and administering an amount of the formulation effective to provide sustained release of the water-soluble molecular compound in the animal for a prescribed period of time.

More particularly, the multi-phase microspheres of the defined method for use in an animal comprise a biodegradable polymer such as PLA or PLGA. The method employs multi-phase microspheres which include any variety of molecular compounds, such as proteins, chemicals, peptides or other pharmacologically active non-toxic drugs.

In a most preferred aspect of the invention, the method includes a water-soluble molecular compound which is active as a therapeutic agent. A microemulsion of an aqueous solution of the water soluble molecular compound in a fixed oil is prepared and then mixed with a polymer solution and dispersion oil medium. No direct contact of organic solvent and the water soluble molecular compound therefor occurs.

Potentially therapeutic molecular compounds which are not stable in water may also be incorporated in the multi-phase microspheres in a method to provide sustained release of the agent in an animal. These types (i.e., unstable in water/subject to water denaturation) may be prepared as already described (e.g., lyophilization mixture of molecular compound in a fixed oil prepared with polymer, solvent and dispersion oil directly, standard preparation with extended drying or hardened microspheres to remove water).

As part of the described method, the particular formulation may be administered intramuscularly or by other parenteral routes. Most preferably, the formulation is administered intramuscularly. It is proposed that delivery of the molecular compound may be achieved for an average of three months in vivo with the described multi-phase microspheres. However, depending on the particular polymer used, the particular molecular compound used, etc., the multi-phase microspheres may be formulated to provide delivery in vivo of the agent for up to 1 year.

In still another embodiment of the present invention, a method for preparing multi-phase microspheres is provided. Most preferably, the claimed method for preparing multi-phase microspheres containing a molecular compound comprises preparing a solution of the molecular compound (in water) with a fixed oil to form a microemulsion, mixing a biocompatible polymer and a polymer solvent together to form a polymer solution, dispersing the microemulsion into the polymer solution to form a W/O/"O" emulsion, mixing the W/O/"0" emulsion together in a dispersion oil which is incompatible with the polymer solvent to form a multiple emulsion, agitating and removing the solvent from the multiple emulsion to form hardened microspheres and washing and drying the hardened microspheres to form multi-phase microspheres containing the molecular compound. So prepared, the described -multi-phase microspheres are suitable for use as a long acting drug delivery device for virtually any protein, peptide, chemical or therapeutic agent. Where the particular molecular compound is unstable in water, the microemulsion may first be lyophilized to remove water and enhance the stability of the molecular compound before mixture with the polymer, polymer solvent and "dispersion" (oil) medium.

Most preferably, the invention provides a method for preparing a multi-phase microsphere containing water-soluble molecular compounds. In this embodiment, an aqueous solution of the water soluble molecular compound is prepared. Where the molecular compound is stable in water, no lyophilization of the microemulsion is required before mixing same in a solution of polymer and solvent in a "dispersion" (oil) medium.

Most preferably, the particular fixed oil of the microemulsion is soybean, safflower, cottonseed, peanut, sesame or cod liver oil. In addition, the microspheres may be most efficaciously prepared with the polymer solvent, acetonitrile. Again, the particular biodegradable polymer preferred for use in the preparation of the described microspheres is PLA or PLGA. Mineral oil would be used as a suitable oil of the "dispersion" medium where the polymer solvent is acetonitrile. Thus, the particular polymer-solvent mixture in a most particularly preferred embodiment of the claimed method is a PLA or PLGA/acetonitrile solution.

As part of the claimed method, the solvent is removed from the W/O/"O" emulsion by the process of evaporation under atmospheric pressure, wherein the microemulsion is subject to constant agitation (i.e., stirring) in the dispersion (i.e., mineral oil) medium. The multi-phase microspheres produced according to the described method are most preferably about 150 microns ($\mu$) in size. Even more preferably, the multi-phase microspheres are to be prepared so as to be between 100–200$\mu$ in size. Most preferably, the multi-phase microspheres may be prepared so as to attain a size of between about 50 microns and about 100 microns by slight modification of the speed or agitation and of the viscosity of the microemulsion/polymer solution system, employing other surfactants, modifying the dilutions of polymer solution employed, and/or increasing the temperature employed during formulation.

In certain preferred embodiments of the described method, the water-soluble molecular compound is a water-soluble protein, peptide, chemical, dye or drug. Examples include brilliant blue, CPM, DPH, PMZ or PRC. Even more preferably, the aqueous phase described in conjunction with the preparation of the multi-phase microspheres includes Tween 80 at about 4% W/W, (or about 1% W/W of the microemulsion). In addition, the oil phase as described in the present methods most preferably includes Span 80, at a concentration of about 5% W/W (or 4% W/W in the W/O emulsion).

In an even more particularly preferred embodiment of the method for preparing multi-phase microspheres containing a water-soluble molecular compound, the method comprises, preparing a first mixture of a water-soluble molecular compound in water, gelatin and Tween 80 to form an aqueous phase, preparing a second mixture of an amount of aluminum stearate (particularly, aluminum monostearate) and a volume of a fixed oil to provide a 2% aluminum stearate and about 5% (4% in the W/O emulsion) W/W of Span 80 oil phase, combining the first mixture with the second mixture to form a coarse W/O emulsion, processing the coarse W/O emulsion into a fine W/O microemulsion, preparing a third mixture of a biodegradable polymer and a polymer solvent, combining a quantity of the fine W/O microemulsion with the third mixture to form a W/O/"O" emulsion, preparing a fourth mixture of an oil incompatible A, with the polymer solvent and an amount of Span 80, pouring the W/O/"O" into the fourth mixture to form a multiple emulsion, agitating and evaporating the solvent from the multiple emulsion to form hardened microspheres, separating the hardened microspheres from the mixture, and washing and drying the hardened microspheres to form multi-phase microspheres containing a water-soluble molecular compound. Most preferably, coarse W/O emulsion is processed to form a fine w/o emulsion by homogenizing the coarse W/O emulsion.

In a particularly preferred embodiment of the claimed method, the third mixture comprises less than 35% W/W of the biodegradable polymer. Even more particularly, the method includes a third mixture which comprises about 33% W/W of a PLA biodegradable polymer in an acetonitrile polymer solvent. Where the biodegradable polymer is PLGA, the third mixture comprises about 31% W/W of PLGA in an acetonitrile solvent. These particular most preferred amounts of biodegradable polymers in a solvent of the third mixture has been found to optimize the loading efficiency of water-soluble molecules in the multi-phase microspheres of the present invention. For example, loading efficiencies of between 80%–100% were obtained using this system and these relative amounts of polymer. Examples of those water-soluble molecules which may be included within the multi-phase microspheres of the present invention are the water-soluble dye brilliant blue and the drugs CPM, DPH, PMZ, and PRC.

The particular emulsion-to-polymer ratio, as well as the concentration of surfactant to be included in the evaporation (i.e., same as the "dispersion" medium) medium (mineral oil), were parameters which the inventors found to affect drug loading efficiencies in each of the preparations. Thus, ratios of these particular components in the microspheres and in the methods for their preparation are important to maximizing drug loading efficiency.

The amount of the W/O emulsion dispersion inside the microspheres has also been observed by the present inventors to affect the loading efficiency of a particular biologically active agent into the microsphere preparation. Thus, the inventors have defined most preferred ranges of the quantity of the W/O emulsion which is to be included within those W/O/"O" emulsions in the current process. Thus, in a most particularly preferred embodiment of the claimed process, the quantity of the fine W/O emulsion (microemulsion) is to be between about 0.25 to 1.0 grams by weight per 1 gram of the polymer contained in the W/O/"O" emulsion.

The inventors have also observed that the loading efficiency of a water-soluble molecular compound into the described multi-phase microspheres is also affected by the percentage (W/W) of Span 80 included within the fourth mixture which includes a fixed oil and an amount of Span 80. The best drug loading efficiencies were observed when the fourth mixture (multiple emulsion) included between about 0.25% to about 2% W/W Span 80. Even more preferable, about 0.25% to 0.5% W/W of Span 80 is to be included within the fourth mixture. Finally, the most preferred concentration of Span 80 to be included within the fourth mixture with a fixed oil is about 0.25% W/W.

While the duration of action of the multi-phase microspheres (i.e., the "in vivo life span") will depend on the properties of the particular biocompatible polymer selected and the rate of biogradation characteristic of the polymer, as well as the stability of the particular water soluble molecular compound incorporated, microspheres prepared according to the presently described system are expected to provide a steady and constant release of a compound for about three months at a time.

Where TNF is the molecular compound incorporated, controlled and constant drug release may be achieved for about 1 month. This time period will depend upon the molecular weight of the polymer used, the site of administration of the multi-phase microspheres, the polymer/drug ratio, the type and rate of degradation of the polymer (PLA>PLGA) used, the particle size of the "microemulsion," and other factors known to those in the art. It is hypothesized that the described multi-phase microspheres may be so formulated so as to highly controlled molecular compound release for up to 1 year in vivo.

BRIEF DESCRIPTION OF THE DRAWINGS

FIG. 2. In vitro dissolution of brilliant blue from multi-phase and (A) and conventional and (B) multi-phase PLGA microspheres containing various amount of the dye. The medium was pH 7.4 phosphate buffered saline, 37° C.

FIG. 2-B demonstrates a typical relatively long lag phase, with virtually no release of brilliant blue for 18 days, followed by a "burst" phase of rapid release after 20 days. The percentage of brilliant blue release increases with the increasing concentration of the brilliant blue in the microsphere (e.g., at 30 days: 40% dissolved brilliant blue release in the 0.2 mg/g brilliant blue microspheres; about 80% dissolved brilliant blue release in the 1.3 mg/g brilliant blue microspheres; about 90% dissolved brilliant blue release in the 2.5 mg/g brilliant blue microspheres).

In FIG. 2-B, the dissolution profile is essentially devoid of a lag phase. About 10% brilliant blue is released after about 3 days from microspheres containing 0.3 mg/g, 0.4 mg/g, 0.8 mg/g or 1.0 mg/g. The percentage of brilliant blue release is demonstrated to be relatively independent of the concentration of brilliant blue in the microsphere.

FIG. 3. In vitro dissolution of CPM from conventional and (A) and multi-phase (B) PLGA microspheres containing various amount of the CPM. The medium was pH 7.4 phosphate buffered saline, 37° C.

FIG. 10. PLGA molecular weight changes of residual beads of multi-phase and conventional microspheres containing brilliant blue (A) and CPM (B) during in vitro dissolution test. The molecular weights were determined by gel permeation chromatography.

FIG. 11. Schematic features of a multi-phase microsphere (A) prepared by a multiple emulsion solvent evaporation technique and a microsphere (B) prepared by a conventional solvent evaporation technique.

FIG. 14. Comparison of drug loading efficiency between multi-phase and conventional PLGA microspheres. Theoretical drug content is shown beside each profile.

DETAILED DESCRIPTION OF THE PREFERRED EMBODIMENTS

Figure 1:
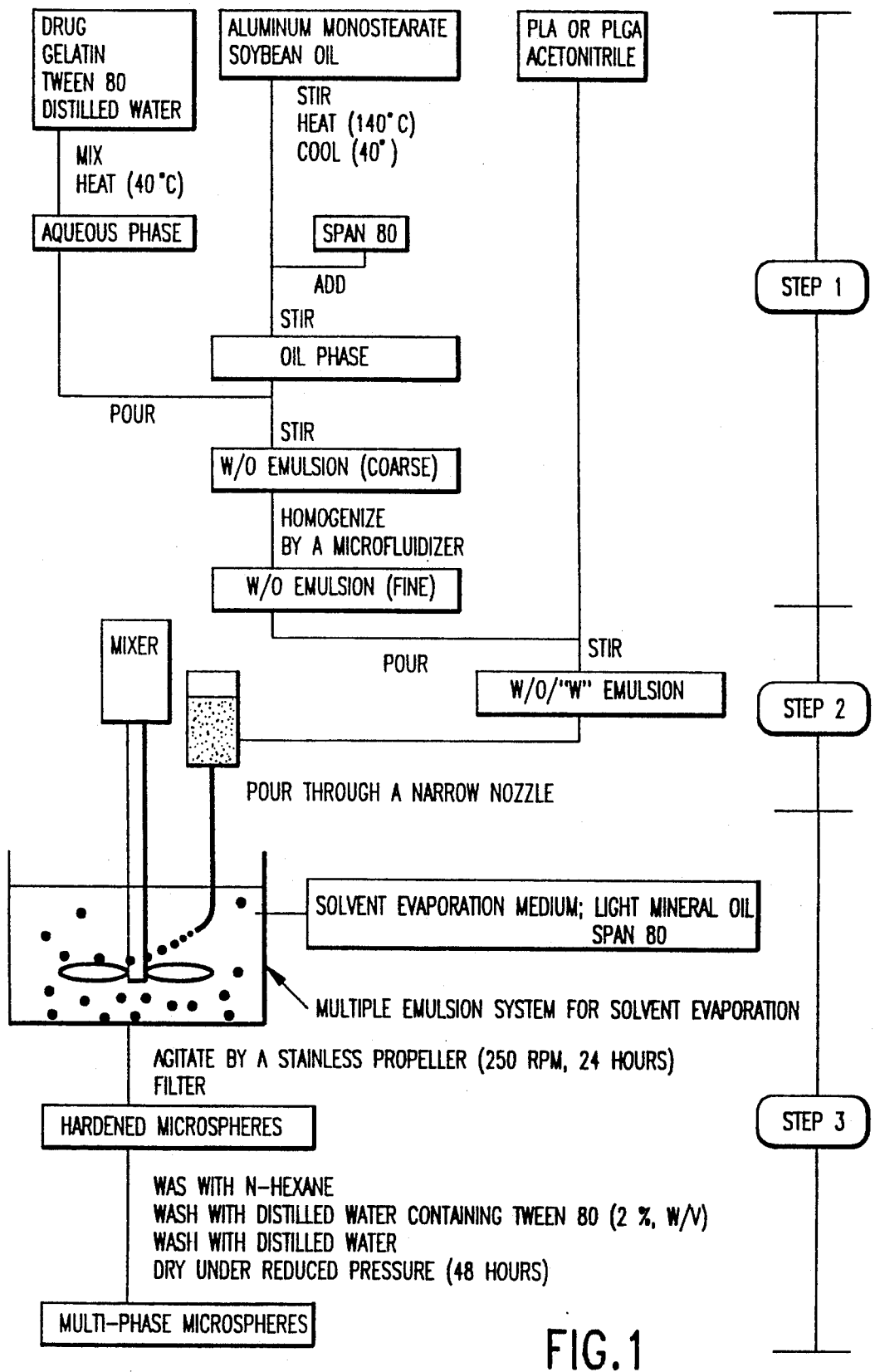
FIG. 1. Preparative method for multi-phase microspheres containing water-soluble drugs by a multiple emulsion solvent evaporation technique.

Novel multi-phase microspheres containing a molecular compound solution-in-oil microemulsion comprise the highly stable and slow releasing multi-phase microspheres of the present invention. The unique water-in-oil microemulsions are employed by the inventors in a multiple emulsion technique in the preparation a hybrid microsphere, defined as multi-phase microspheres. These multi-phase microspheres include numerous, tiny microemulsions in the form of oily droplets dispersed throughout a biodegradable polymer matrix. This technique innovatively provides for the elimination of contact between the polymer and the molecular compound, as well as enhancing the slow release characteristic of the compound from the microsphere.

The elegant design of the compositions (i.e. multiphase microspheres) and methods employing the compositions disclosed herein circumvent technical problems associated with microspheres and microcapsules described in the art, as well as those technical difficulties associated with providing efficient incorporation of a water soluble component in a drug delivery system. For example, the slow release action of the presently disclosed multi-phase microspheres make possible the design of in vivo treatment regimens which are effective over therapeutically valuable and/or necessary treatment periods. The present methods also eliminate the necessity of multiple injections and/or administration of the particular pharmaceutical. In addition, the unique "microemulsion" design included in the claimed multi-phase microspheres provides for high water soluble molecule loading efficiency without loss of slow and constant control of drug release, as compared to the content-dependent rate of drug delivery observed in conventional microsphere systems.

The methods of the present invention provide for a uniquely modified multiple emulsion system as part of the solvent evaporation step in multi-phase microsphere preparation. Specifically, conventional "O"/O (acetonitrile-in-mineral oil) emulsions of polymer acetonitrile solution and molecular compounds directly is replaced by a multiple emulsion system wherein the molecular compound is first separately emulsified with a fixed oil, which is then combined with a polymer-in-solvent combination in the presence of a dispersion medium of an oil incompatible with the polymer solvent. Thus, during the solvent evaporation process, the molecular compound is prevented from diffusing into an outer phase of the emulsion system.

Multiple emulsion systems with organic solvents have been described with some limited degree of success.[21] However, because a "microemulsion" of an aqueous solution of the drug in an oil, or of a drug in an oil (in the case of water-insoluble molecular compounds) is not employed as part of the preparation, the protein or enzyme is left in direct contact with the polymeric materials employed. Thus, the molecular compounds of such systems would be subject to denaturation/degradation through polymer contact, contact with a surfactant, organic solvent residuals and contact with organic solvents (e.g. acetonitrile). The potential for this type of degradation is eliminated through use of the disclosed methods, thus making microsphere delivery of potent and costly synthetic proteins and peptides a commercially feasible option.

The presently described compositions and methods may be used with both water soluble molecular compounds and molecular compounds which are unstable in aqueous solutions. Denaturation of molecular compounds which are unstable in water may be prevented by either first lyophilizing the microemulsion of the aqueous solution of the molecular compound in oil before the "dispersion" thereof in a solution of polymer and solvent and a dispersion oil, or by simply drying the final microspheres under a vacuum to remove water from the microspheres. Alternatively, the drug may first be dispersed within a fixed oil containing aluminum monostearate, and the drug-oil mixture combined with a polymer plus polymer solvent solution and a "dispersion" oil.

Poly(d,l-lactic-co-glycolic acid)(MW 57,000 lactide/glycolide =50/50) was purchased from Birmingham Polymers, Inc. (Birmingham, Ala.). Purified gelatin and acetonitrile was purchased from Fisher Scientific Co. (Fairlawn, N.J.). Brilliant blue FCF was obtained from Allied Chemical Co. (New York, N.Y.). Soybean oil, light mineral oil (USP) and aluminum monostearate (USP/NF) were purchased from Spectrum Chemical Mfg. Co. (Gardena, Calif.). Sorbitan monooleate (SPAN 80) and polyoxyethylene sorbitan monooleate (Tween 80) were obtained from ICI Americas Inc. (Wilmington, Del.).

Poly(d,l) lactic acid (Mw 100,000) was also obtained from Birmingham Polymers Inc. (Birmingham, Ala.). d,l-Chlorpheniramine maleate, procainamide hydrochloride, and promazine hydrochloride were obtained from Sigma Chemical Co. (St. Louis, Mo.). Diphenhydramine hydrochloride (USP/NF) was also obtained from Spectrum Chemical Mfg. Co. (Gardens, Calif.). Recombinant human tumor necrosis factor (TNF) was obtained from Dainippon Pharmaceutical Co., Ltd. (Osaka, Japan).

Even though the invention has been described with a certain degree of particularity, it is evident that many alternatives, modifications, and variations will be apparent to those skilled in the art in light of the foregoing disclosure. Accordingly, it is intended that all such alternatives, modifications, and variations which fall within the spirit and scope of the invention be embraced by the defined claims.

The following examples are presented to describe preferred embodiments and utilities of the present invention, but should not be construed as limiting the claims thereof.

Example 1—Preparation of Multi-phase Microspheres

Example 2—Water-Soluble Molecular Compound Loading Efficiencies with TNF—Comparison between Multi-phase and Conventional Microspheres.

Example 3—Microsphere Formation and Drug Loading Efficiencies with Water-Soluble Molecular Compounds with Varying PLA and PLGA Polymer Concentrations.

Example 4—Microsphere Water Soluble Molecular Compound Loading Efficiency and Span 80 Concentration.

Example 5—Comparison of Drug Loading and of In Vitro Dissolution in Conventional vs. Multi-phase Microspheres with CPM and Brilliant Blue.

Example 6—Comparison of Loading Efficiencies, Release Properties and Morphology of Conventional and Multi-phase PLGA Microspheres with CPM, DPH, PMZ, PRC and Brilliant Blue.

Prophetic Example7—Proposed Methods for Preparing Multi-Phase Microspheres with Water-Soluble Peptides and Proteins and Multi-phase Microspheres of Less than 150μ Size.

EXAMPLE 1

Preparation of Multi-phase Microspheres

The present example is provided to demonstrate one particularly preferred method by which the multi-phase microspheres of the present invention may be prepared with virtually any molecular compound. The multi-phase microspheres prepared in the present example were found to have a particle size of between about 150μ to 300μ. However, particles of smaller size (e.g., between 50μ to 100μ, less than 150μ) may be obtained through modifying the presently described system as outlined in Prophetic Example 7.

Molecular compounds that are soluble and stable in water (e.g. CPM, PMZ, DPH, PRC) may be prepared as an aqueous solution, which is then dispersed in an oil to form a microemulsion. Molecular compounds which are unstable (subject to denaturation in a water mixture with an organic solvent) (e.g., TNF), the final microspheres may be dried under vacuum to remove the water from the microspheres. Alternatively, a water/oil microemulsion of the drug may be prepared and the microemulsion lyophilized to remove or decrease the water content prior to emulsification in the dispersion oil and acetonitrile-polymer solution. This system would result in finely dispersed particles of the drug in the oil phase prior to the encapsulation process.

For organic molecules that readily decompose or denature in the presence of moisture, these agents should be finely dispersed in the fixed oil prior to dispersing the oil in the acetonitrile solution of the polymer.

The multi-phase microspheres were prepared by a multi-phase solvent evaporation process. The three-step emulsification process is described in FIG. 1. The preparation of the W/O emulsion (aqueous solution of a water-soluble molecular compound in a fixed oil (e.g., soybean oil or safflower oil)) constitutes step 1. This results in a unique "microemulsion" of the oil and the compound contained within a number of fine droplets.

The W/O-in-acetonitrile (W/O/"O") emulsion was prepared by dispersing the W/O emulsion in the polymer-acetonitrile solution as outlined in step 2. The polymer solvent, acetonitrile, was removed from the W/O/"O" emulsion by evaporation under atmospheric pressure. In order to achieve the finished product represented in step 3, the hardened microspheres were placed under reduced pressure for complete removal of the acetonitrile. Formulations for the microspheres containing molecular compounds in the emulsion system are shown in table 1.

TABLE 1

| The Formula For Multi-Phase Microspheres | | | |
|---|---|---|---|
| Phases | Elements | Theoretical amounts (mg) | |
| Core (W/O emulsion) | Water | Brilliant blue (or CPM) | 1.07 (30.5) |
| | | Gelatin | 0.83 |
| | | Tween 80 | 3.33 |
| | | Distilled Water | 79.14* |
| | Oil | Aluminum monostearate | 5.00 |
| | | Span 80 | 10.00 |
| | | Soybean oil | 235.00 |
| Wall Polymer | PLGA or PLA | | 666.70 |
| Total weight | | | 1000.00 |

More specifically, the soybean oil in step 1 (FIG. 1) was heated to 140° C/ to dissolve the aluminum stearate (2% w/w), after which the oil phase was cooled to 40° C. The aqueous phase (25 ml) containing the water-soluble molecular compound, in this case brilliant blue or CPM, and gelatin (1% w/w), and Tween 80 (4% w/w) was poured into the oil phase (75 ml) containing Span 80 (4% w/w) and agitated in order to obtain a coarse W/O emulsion. The W/O emulsion was then homogenized with a microfluidizer (model M-110T) until a fine microemulsion was obtained.

In step 2, the polymer and polymer solvent solution was added. PLA or PLGA are the preferred biodegradable polymers. Each of these polymers (about 3 grams) were first dissolved in a volume of acetonitrile (about 4 grams, Fischer Scientific Co.). The W/O microemulsion (drug gelatin, Tween 80, Span 80, soybean oil, aluminum stearate) was poured int this polymer-acetonitrile solution and dispersed to form a W/O/"O" emulsion (multiple emulsion).

It was noted that at the final drying step under reduced pressure (48 hrs) (Step 3, FIG. 1), there may occur "dehydration" of the water/oil emulsion incorporated in the multi-phase microspheres.

In step 3, the W/O/"O" emulsion was poured gently through a narrow nozzle into agitated light mineral oil containing Span 80 to form a W/O/"O"/O multiple emulsion (the "dispersion" medium). The multiple emulsion system was agitated by a stainless steel propeller for 24 hours to evaporate and remove the acetonitrile. The hardened microspheres were filtered using nylon screens; washed with n-hexane, Tween 80 solution (2% w/v) and distilled water. For further solvent removal, the microspheres were dried under reduced pressure for 48 hours. The schematic features of the multi-phase microsphere preparation protocol are illustrated in FIG. 1.

Adjustment of Preparative Conditions for Multiple Emulsion Solvent Evaporation

Span 80 and Tween 80 were used as emulsifying agents to make a water (aqueous water soluble molecular compound solution) in soybean oil (W/O) emulsion. This W/O emulsion was found to be unstable in the PLA or PLGA-acetonitrile solutions (step 2), and the aqueous phase of the emulsion was readily released into the acetonitrile solution due to phase inversion. The addition of aluminum monostearate to soybean oil was effective in preventing phase inversion with the W/O emulsion by increasing the viscosity and plasticity of the soybean oil. Aluminum monostearate has been previously used as a hardening agent for oils in non-aqueous penicillin G suspensions for injections. The levels of Span 80 and Tween 80 were optimized to decrease the size of the aqueous phase in the W/O emulsions prepared by homogenization.

EXAMPLE 2

Molecular Compound Loading Efficiencies with TNF-Comparison Between Multi-phase Microspheres and Conventional Microspheres The present example is provided to demonstrate the applicability of the presently disclosed multi-phase microsphere system for use with virtually any protein which is not necessarily stable in the aqueous phase of a "W/O" emulsion which contacts with a polymer solvent, such as acetonitrile. The multi-phase microsphere system of the present example employs TNF as an exemplary protein.

Multi-phase TNP Microspheres

TNF is a molecular compound which is unstable in water, and which will become denatured if placed in an aqueous phase of a "W/O" emulsion in an acetonitrile-polymer solution. This is because the outer acetonitrile will penetrate into the aqueous phase. Multi-phase microspheres were prepared by first preparing a TNF solution, emulsifying the TNF solution in cyclohexane, and lyophilizing the emulsification to form a fine powder. This powder was dispersed in the oil containing aluminum monostearate. This oil suspension was then used for the preparation of the multi-phase microspheres of TNF.

Alternatively, a microsphere may be prepared substantially according to the steps outlined in FIG. 1, except that the final microspheres must be dried under vacuum to remove the water from the microspheres, thus enhancing the stability of the TNF.

Conventional TNF Microspheres

Conventional microspheres with TNF were prepared by dissolving the TNF in a polymer and acetonitrile solution to provide a mixture. The mixture was then poured into mineral oil containing Span 80 through a narrow nozzle, and agitated for 48 hours with a stainless steel propeller. After this stage, the obtained microspheres were processed by substantially the same remaining steps outlined in FIG. 1 (step 3, FIG. 1).

Because TNF is denatured in the presence of water, the final product microspheres of both the multi-phase and conventional microspheres should be free of moisture in order to maintain the stability of the protein.

The amount of TNF employed in the microspheres of the present example was about 5 mg.

TNF employed for preparing both the convention and multi-phase microspheres was obtained from Dainippon Pharmaceutical Co., Ltd., Osaka, Japan, recombinant human tumor necrosis factor. TNF has a molecular weight of 18,000 and an isoelectric point of 5.9. The TNF of the present example is stable at pH 6 to 9.

The above-described multi-phase and conventional microspheres were prepared using the biodegradable polymer PLGA. Microspheres prepared in batch 1 and batch 2 both employed the same lot of TNF obtained from Dainippon Pharmaceutical Co.

The loading efficiency of TNF into multi-phase and conventional (i.e., matrix) microspheres was measured and compared. The data obtained is presented in Table 2.

TABLE 2

Comparison of TNF loading efficiency between multi-phase and conventional microspheres.

| Type of microspheres parameter | Batch*1 number | Particle size range D | Loading efficiency E % | Weight Fraction W |
|---|---|---|---|---|
| Multi-phase | 1 | 100–250 μm | 78.5% | 0.474 |
| | | 250–500 | 100.2 | 0.526 |
| | | 100–500 | 89.9*2 | 1.000 |
| | 2 | 100–250 | 85.5 | 0.757 |
| | | 250–500 | 99.8 | 0.243 |
| | | 100–500 | 88.9*2 | 1.000 |
| | over all | 100–250 | 82.0*3 | 0.616 |
| | mean of | 250–500 | 100.3*3 | 0.384 |
| | 1 and 2 | 100–500 | 89.4*3 | 1.000 |
| Conventional | 1 | 100–250 μm | 53.6% | 0.478 |
| | | 250–500 | 70.6 | 0.522 |
| | | 100–500 | 69.8*2 | 1.000 |
| | 2 | 100–250 | 68.7 | 0.594 |
| | | 250–500 | 71.6 | 0.405 |
| | | 100–500 | 62.5*2 | 1.000 |
| | over all | 100–250 | 61.2*3 | 0.536 |
| | mean of | 250–500 | 71.1*3 | 0.464 |
| | 1 and 2 | 100–500 | 66.2*3 | 1.000 |

*1 Solvent evaporation (step 3) was carried out at agitating speed at 400 rpm (batch-1) and 500 rpm (batch-2).
*2 Loading efficiency (100–500 um) was calculated as follows:
$$E \%(100\text{--}500) = \frac{E \%(100\text{--}250) \times F(100\text{--}250) + E \%(250\text{--}500) \times F(250\text{--}500)}{F(100\text{--}250) + F(250\text{--}500)}$$
*3 Loading efficiency (a–b μm) was calculated as follows:
$$E \%(a\text{-}b) = \frac{(E \%(a\text{-}b) \text{ of batch-1}) + (E \%(a\text{-}b) \text{ of batch-2})}{2}$$

The TNF loading efficiency in batch 1 of the multi-phase microspheres was 89.9%, while TNF loading efficiency for batch-2 multi-phase microspheres was 88.9%. The mean TNF loading efficiency into multi-phase microspheres of both batch 1 and batch 2 preparations was 89.4%. The TNF loading efficiency observed in conventional (matrix-type) microspheres, batch 1 was 69.8%. TNF loading efficiency in batch 2 conventional (matrix) microspheres was 62.5%. The average TNF loading efficiency into conventional (matrix) microspheres was 66.2%. These data demonstrate a significant enhancement in TNF loading efficiency using multi-phase microspheres, as compared to conventional matrix type microsphere systems.

Batch 1 microspheres were prepared using an agitating speed of 400 rpm at step 3 (see FIG. 1). Batch 2 microspheres were prepared at an agitating speed of 500 rpm at step 3 (see FIG. 1). The same lot of TNF obtained from Dainippon Pharmaceutical Co. Ltd. was used in the preparation of both batches of TNF microspheres.

EXAMPLE 3

Microsphere Formation and Loading Efficiencies With Water-soluble Molecular Compounds With Varying PLA and PLGA Concentrations The present example is provided to demonstrate the effect of polymer concentrations on microsphere formation and on the optimization of microsphere drug loading efficiency and the dependence thereon on particular polymer concentrations.

The effect of changes of PLA and PLGA concentrations in acetonitrile (polymer solvent) on microsphere drug loading efficiency and the appearance of multi-phase microspheres was studied. A concentration of 0.25% w/w of Span 80 was included in the "dispersion" medium of light mineral oil and Span 80. The steps for preparing the microspheres were substantially the same as that outlined in FIG. 1.

Microsphere Formation and Polymer Concentration

Spherical multi-phase microspheres were obtained at PLA/acetonitrile concentrations between 28.6 and 33.3% w/w and at concentrations between 22.2 and 30.8% w/w for the PLGA. No aggregation of the particles was observed between these ranges of polymer concentrations.

At low (below about 22.2% for PLA, below about 16.7% for PLGA) concentrations of PLA or PLGA in acetonitrile, it was difficult to disperse the W/O emulsions (the microemulsion) into the polymer solution, and therefore multi-phase microspheres containing the W/O emulsions were not obtained.

As the concentration of the polymers in acetonitrile increased to at least about 16% (the lowest limit being about 22.2% for PLA and about 16.7% for PLGA), dispersion of the W/O emulsion (microemulsion) droplets in the polymer-acetonitrile solution improved. This was attributed to a synergistic effect of the surface-protecting characteristics of the polymer, increased viscosity of the polymer/acetonitrile solution, and cancellation of the density difference between the W/O emulsion (microemulsion) and the acetonitrile medium by the addition of the polymer. At high polymer concentrations, the microspheres aggregated during the process of the solvent evaporation (FIG. 1, step 3). Relatively large and viscous polymer-acetonitrile solution droplets containing the W/O emulsions resulted in irregularly shaped unhardened masses. These masses were observed to cause adhesion to other masses and unhardened microsphere beads.

The highest polymer concentrations in acetonitrile that could be used without aggregation occurring were about 33.3% w/w and about 30.8% w/w for the PLA and the PLGA, respectively. These polymer concentrations were selected in order to minimize the acetonitrile evaporation time.

Figure 12:
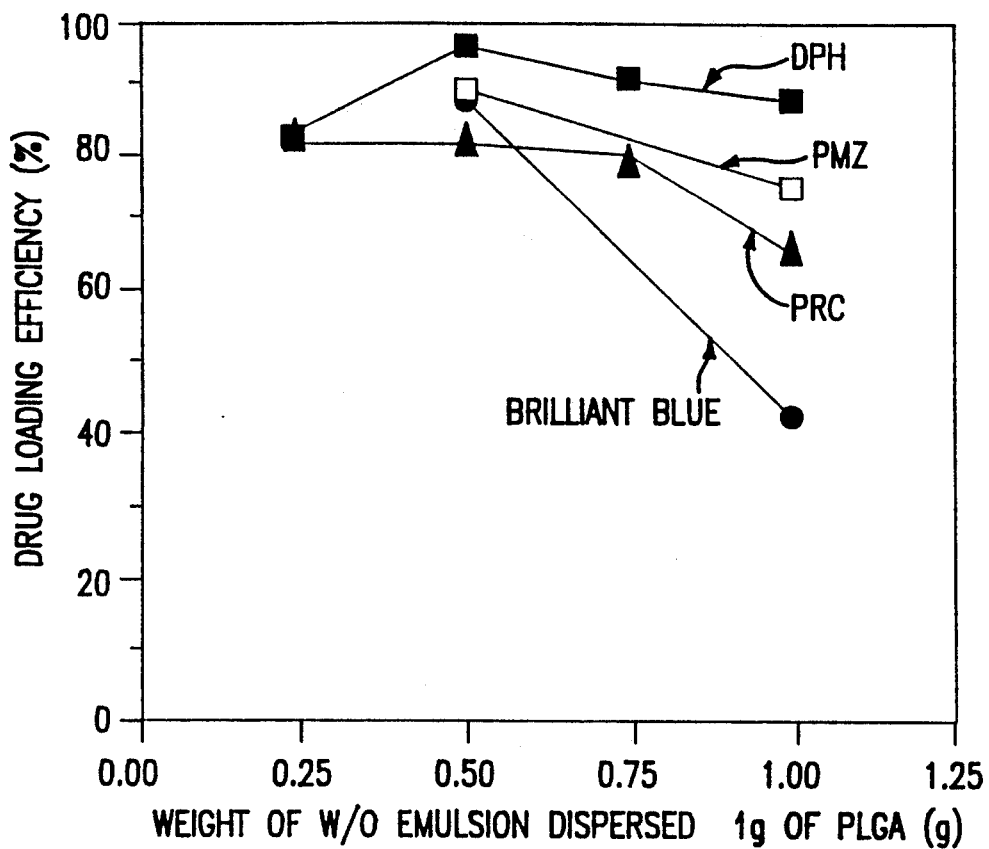
FIG. 12. Drug loading efficiency of multi-phase PLGA microspheres as a function of the level of W/O emulsion dispersed in 1 gram of the polymer.

Water-Soluble Molecular Compound Loading Efficiency and Polymer Concentration Loading efficiencies of brilliant blue, DPH, PMZ, and PRC into the multi-phase microspheres were examined with various amounts of the W/O emulsions (microemulsion) dispersed in 3.25 g of PLGA-acetonitrile solution (30.8% w/w) containing 1.00 g of PLGA. The results in FIG. 12 depict the drug loading efficiencies versus the weight of the W/O emulsions when the multi-phase microspheres were prepared using light mineral oil (the "dispersion" medium) containing 0.25% of Span 80. The W/O emulsion weights ranging from 0.25 to 0.75 g gave relatively high loading efficiencies ($\geq 80\%$).

Drug loading efficiency levels in excess of 70% were obtained with W/O emulsion weights up to 1.00 gram) when DPH, PMZ, and PRC were loaded into the multi-phase microspheres. However, the loading efficiency of brilliant blue decreased significantly when the weight of the W/O emulsion increased to 1.0 g.

The water in the internal aqueous phase of the W/O emulsions began to diffuse into the surrounding polymer-acetonitrile phase as the quantity of the W/O emulsion in the PLGA-acetonitrile solution increased to above 0.5g. This occurred during the agitation steps in the process, resulting in an increase in solubility of the water-soluble molecule molecular compounds DPH, PMZ, and PRC into the surrounding polymer-acetonitrile phase. During the solvent evaporation process, the drug compounds that diffused into the polymer-acetonitrile phase diffused out of the unhardened multi-phase microspheres.

The inventors postulate that the higher water content (93.7% w/w) in the aqueous phase of the W/O emulsion containing brilliant blue precipitated a significant loss in drug loading efficiency. The loading efficiencies of DPH, PMZ, and PRC were reduced only slightly by the increasing amounts of the W/O emulsions, which contained 44.5, 47.3, and 41.1% w/w of water in their aqueous phases, respectively. The percentage of water is limited by the saturation concentration of drugs or compounds. Most preferably, the percent of water (w/w) to be included in the aqueous phase of water soluble drugs should not exceed 50% for optimal drug loading efficiency.

EXAMPLE 4

Water Soluble Molecular Compound Loading Efficiency and Span 80 Concentration The present example is provided to demonstrate the effect of varying concentrations of Span 80 in the "dispersion" media on the drug loading efficiency of water soluble molecular compounds into the multi-phase microspheres of the present invention. The microspheres were prepared according to the protocol outlined in FIG. 1.

Figure 13:
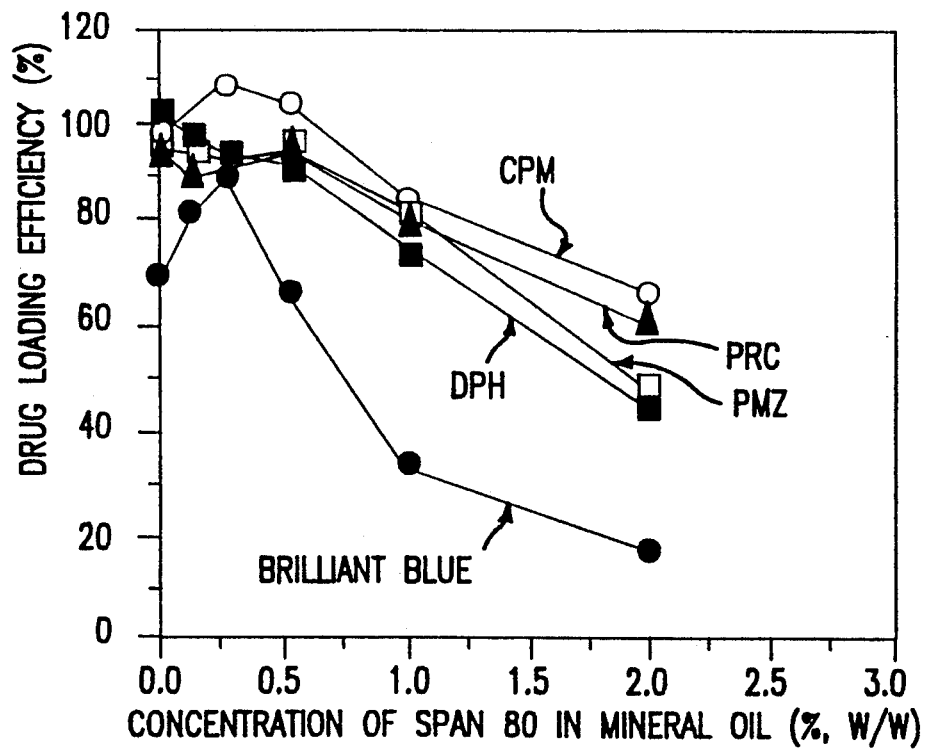
FIG. 13. Influence of the level of Span 80 in mineral oil ("dispersion medium") on the drug loading efficiency of multi-phase PLGA microspheres.

The loading efficiency of brilliant blue, CPM, DPH, PMZ, and PRC in PLGA multi-phase microspheres prepared in mineral oil (dispersion media) containing various concentrations of Span 80 is shown in FIG. 13.

The loading efficiency of brilliant blue had a maximum value of about 904 at 0.25% w/w of Span 80 and decreased significantly at concentrations of Span 80 above 0.5% w/w. Within the Span 80 concentrations ranging from 0.25 to 0.5% w/w, the loading efficiencies of the drugs DPH, PMZ, PRC and CPM exceeded 90% and gradually decreased to 50-70% as the Span 80 concentrations increased to 2.0% w/w.

The optimum concentration of Span 80 for this system was between 0.25 and 0.5% w/w for 804 or greater drug loading efficiency. The loading efficiency reductions, which were observed with each of the tested drugs, were attributed to the increased solubilizing properties of the evaporation (i.e., "dispersion") medium containing above 0.50% of w/w Span 80.

When the concentration of Span 80 was less than 0.25% w/w, the dispersed droplets of PLGA-acetonitrile solution, including the W/O emulsion of brilliant blue and CPM, were unstable, resulting in fusion and agglomeration of the droplets and a decrease in the loading efficiencies of brilliant blue and CPM. The W/O emulsions containing brilliant blue and CPM were disrupted due to the physical stresses of fusion and agglomeration. The loading efficiencies of microspheres containing CPM and DPH exceeded 100% at low concentrations (less than 0.25% w/w) of Span 80. This was due to the removal, during the "separation" and "drying" stages in the process (see FIG. 1), of the PLGA beads that were too small to contain the W/O emulsion. Polymer beads are not able to incorporate W/O emulsion droplets which are larger than the beads themselves. Such "too small" polymer beads pass through a nylon screen and are removed from the products (step 3). Thus, the final products have an increased amount of the W/O emulsion in them.

The microspheres containing other drugs (PMZ, PRC) did not show the drug loading efficiency loss or significant aggregation at the low (0.25% or less) concentrations of Span 80. The mineral oil (dispersion medium) obtained after solvent evaporation of brilliant blue containing multi-phase microspheres was clear, and the released brilliant blue was completely solubilized. However, when CPM, DPH, PMZ, and PRC were loaded in the microspheres, small quantities of crystals or solid drug particles of the drugs appeared in the mineral oil and precipitated with the microspheres at each concentration level of span So in the mineral oil. The theoretical content of brilliant blue, CPM, DPH, PMZ and PRC in the microspheres was 1.07, 30.5, 44.5, 47.3, and 41.6 mg/g, respectively.

The hardened microspheres prepared with a mineral oil and >0.254 Span 80 dispersion medium demonstrated a reduced loading efficiency of brilliant blue.

The other drug diffusion rates from the unhardened microspheres were not influenced by the Span 80 concentration in the mineral oil. In contrast to the brilliant blue, the solubilities of the DPH, PMZ, PRC, and CPM drugs in the mineral oil phase were lower than the concentration of the drugs that diffused out of the unhardened microspheres. This allowed the drug crystal precipitation to act as a rate limiting step and to restrict the diffusion of drug from unhardened microspheres into the mineral oil.

EXAMPLE 5

Comparison of Drug Loading and In Vitro Dissolution in Conventional VS. Multi-phase Microspheres With CPM and Brilliant Blue The present example is provided to demonstrate and compare the dissolution properties and drug loading efficiencies of conventional microspheres and multi-phase microspheres which contain either a water-soluble drug, such as CPM (chlorpheniramine maleate) or a water-soluble dye, such as brilliant blue. The particular water-soluble drug CPM and water-soluble dye, brilliant blue, are used to demonstrate the applicability of employing the disclosed multi-phase microspheres with virtually any water-soluble drug, protein, peptide or dye.

Multi-Phase Microspheres

Multi-phase microspheres of poly (d,l-lactic acid) (PLA) or poly (d,l-lactic co-glycolic acid) (PLGA) containing a water soluble molecular compound solution in oil (W/O) emulsion were prepared by the multiple emulsion solvent evaporation technique described in Example 1. Either CPM or brilliant blue was employed as the water-soluble molecule, to which was added gelatin (about 1% W/V in aqueous phase, Fisher Scientific Company), Tween 80 and distilled water. The fixed oil with which the water-soluble molecular compound was mixed was soybean oil. The soybean oil also included an amount of about 2.0% W/W aluminum monostearate to which about 4% w/w Span 80 was added in about 93.5% soybean oil. The above two -mixtures were combined and agitated to form a "microemulsion".

The polymer/solvent mixture was then prepared, into which the "microemulsion" was poured and mixed together in a dispersion medium of mineral oil and Span 80. Acetonitrile was used as the polymer solvent. A mixture of light mineral oil and Span 80 was employed as the dispersion medium.

The polymeric multi-phase microspheres contained oil-drug reservoirs throughout the polymer matrix, with the water-soluble drug being contained within an aqueous dispersed phase inside the oily droplet.

Conventional Microspheres

Conventional PLGA microspheres containing either CPM or brilliant blue were prepared by an acetonitrile-in-oil (W/O) emulsion solvent evaporation technique substantially as described by Jalil and Nixon[3,4]. The CPM and the PLGA were dissolved in the acetonitrile ("W" phase). Similarly, a preparation of brilliant blue and PLGA were dissolved in acetonitrile. Light mineral oil was used as the evaporation (dispersion) medium in both preparations (O phase). So formed, the resulting conventional CPM or brilliant blue containing microspheres were prepared to provide contact with the polymer matrix.

A. Comparison of brilliant blue and CPM drug loading efficiency and dissolution characteristics of multi-phase and conventional microspheres 1. Drug Loading Efficiency The drug loading efficiencies of brilliant blue and CPM in multi-phase and conventional microspheres are shown in FIG. 14. Approximately the same theoretical levels of both agents were loaded into preparations by each process. The drug loading efficiencies of the multi-phase microspheres were higher than those of the conventional microspheres prepared from acetonitrile and mineral oil.

Minuscule levels of water-soluble CPM and brilliant blue were found when the microspheres were prepared using the traditional non-aqueous (drug/acetonitrile solution-in-mineral oil) ("W"/O) system. In contrast, the loading efficiency of CPM in particular was significantly higher in the multi-phase microspheres than in the conventional microspheres (FIG. 14-B) (Multi-P=100% loading eff. vs. Cony.=about 40% loading eff.).

The drug loading efficiencies of both types of microspheres decreased when less than or 0.25% W/W of Span 80 was added to the mineral oil dispersion medium. However, 0.251% Span 80 (W/W) was found by the present inventors to provide acceptable results. The multi-phase microspheres effectively prevented both brilliant blue and CPM from "leaking out" into the mineral oil during the solvent evaporation process. Since the polymer walls were in the liquid state, the drug (CPM), which was trapped in the W/O emulsion consisting of a hardened oil phase, diffused out into the evaporation medium at a much slower rate than the drug that was dispersed in the unhardened conventional microspheres.

2. Dissolution Study of CPN or Brilliant Blue in conventional vs multi-phase microspheres Dissolution rate results observed with the brilliant blue and CPM in the conventional and multi-phase microspheres appear to be the same. Later onset of rapid dissolution with multi-phase microspheres and CPM provide a slower drug release system suitable for protracted drug delivery regimens. The onset of rapid dissolution was relatively the same as between conventional and multi-phase microspheres containing water-soluble brilliant blue dye.

However, the onset of most rapid dissolution of water-soluble drug (CPM)-containing microspheres was almost the same in multi-phase (18.4 (day)) as compared to convention (19.6 day) microspheres. The dissolution rate results observed with the brilliant blue and CPM in conventional and multi-phase microspheres appear in Table 3.

TABLE 3

Dissolution Study of CPM or Brilliant Blue in Microspheres
The estimated onsets of rapid dissolution of brilliant blue and CPM from multi-phase and conventional microspheres.

| Water-soluble substances | Types of microspheres | Content (mg/g) | Estimated onsets for the rapid dissolution (day) | |
|---|---|---|---|---|
| Brilliant Blue | Conventional | 0.2 | 21.7 | 22.15 (mean) |
| | | 1.3 | 22.6 | |
| | Multi-phase | 0.3 | 22.9 | 21.6 (mean) |
| | | 0.4 | 22.7 | |
| | | 0.8 | 20.7 | |
| | | 1.0 | 20.1 | |
| CPM | Conventional | 41.3 | * | 19.6 |
| | | 60.1 | * | |
| | | 127.7 | 19.6 | |
| | Multi-phase | 6.7 | 17.6 | 18.4 (mean) |
| | | 14.4 | 19.6 | |
| | | 27.5 | 18.6 | |
| | | 38.6 | 18.1 | |

*Onset for rapid release was not observed.

Figure 8A:
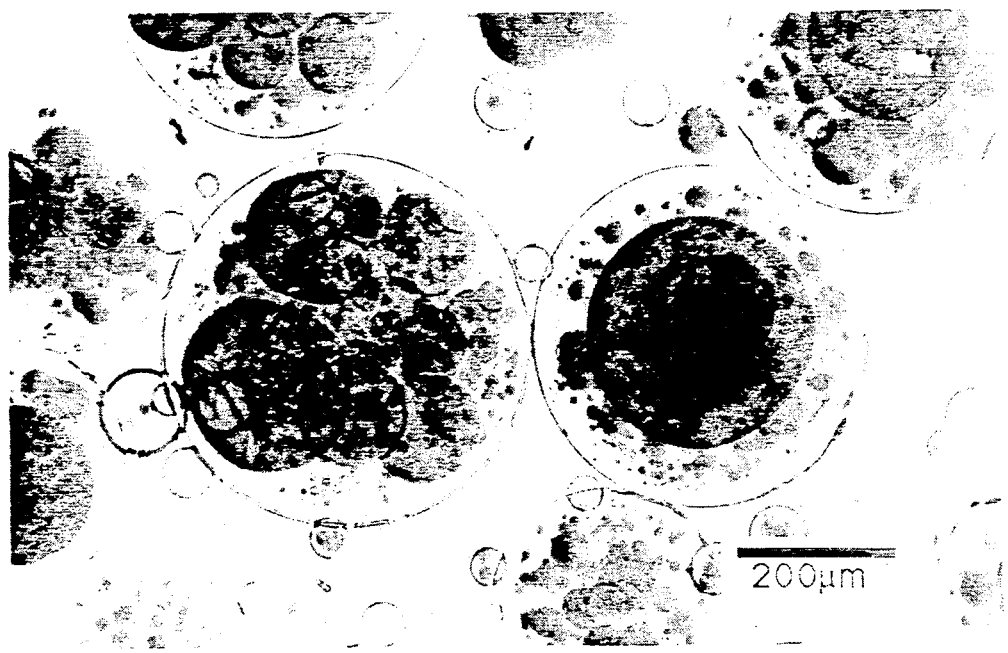
FIG. 8. Photographs taken under transmitted light of multi-phase PLGA microspheres containing brilliant blue prepared by a multiple emulsion solvent evaporation technique (A) and conventional PLGA microspheres containing brilliant blue prepared by a W/O emulsion solvent evaporation technique (B).
Figure 8B:
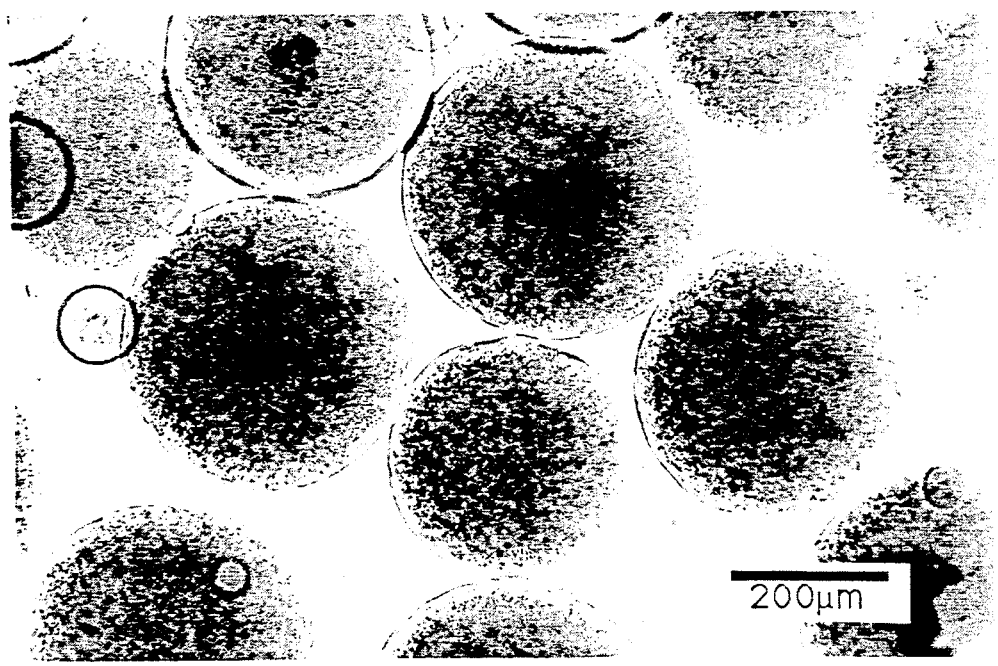

B. Comparison of Brilliant Blue and CPM Morphology of Multi-Phase and Conventional Microspheres A micrograph of the PLGA multi-phase microspheres containing brilliant blue, as observed by transmitted-light, is shown in FIG. 8-A. The dark areas in the microsphere beads are the W/O emulsions containing brilliant blue. Scattered fine particles seen in the polymer wall are brilliant blue particles that have leaked out of the W/O emulsions. Cavities were observed in the cross sections of the microspheres under reflected light conditions. These results demonstrate that the multi-phase microspheres belong to a class of hybrid matrix type drug delivery devices not before recognized. The distribution of the dye in the PLGA microspheres prepared by the conventional method is seen in FIG. 8-B.

Figure 5A:
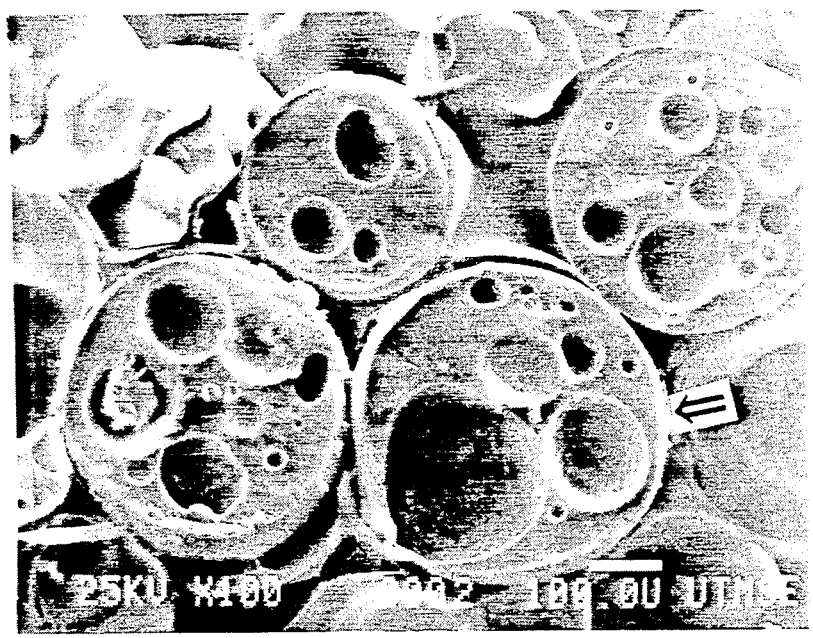
FIG. 5. PLGA multi-phase microspheres with brilliant blue after 1 week in vivo dissolution. Cross section =A, outward appearance =B.
Figure 5B:
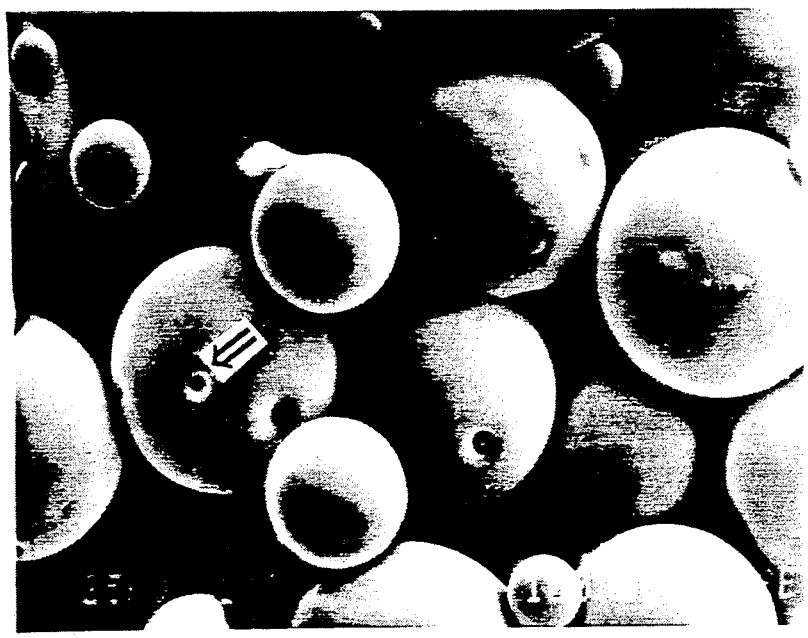
Figure 6A:
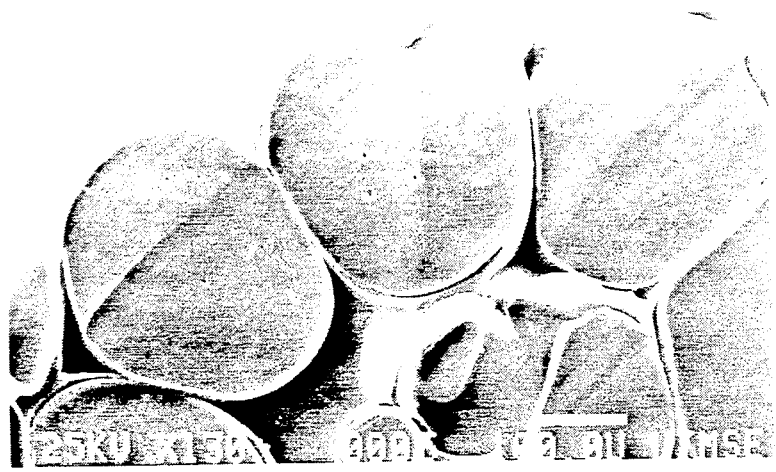
FIG. 6. Morphological changes of conventional PLGA microspheres containing brilliant blue during an in vitro dissolution test. The samples (initial (A)) were observed after a week (B), 2 weeks (C) and 4 weeks (D) by scanning electron microscopy.
Figure 6B:
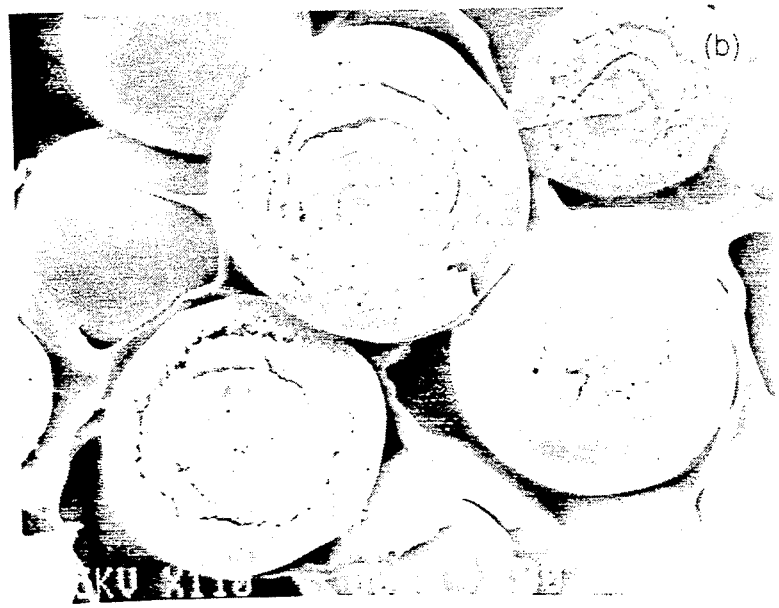
Figure 6C:
Figure 6D:
Figure 7A:
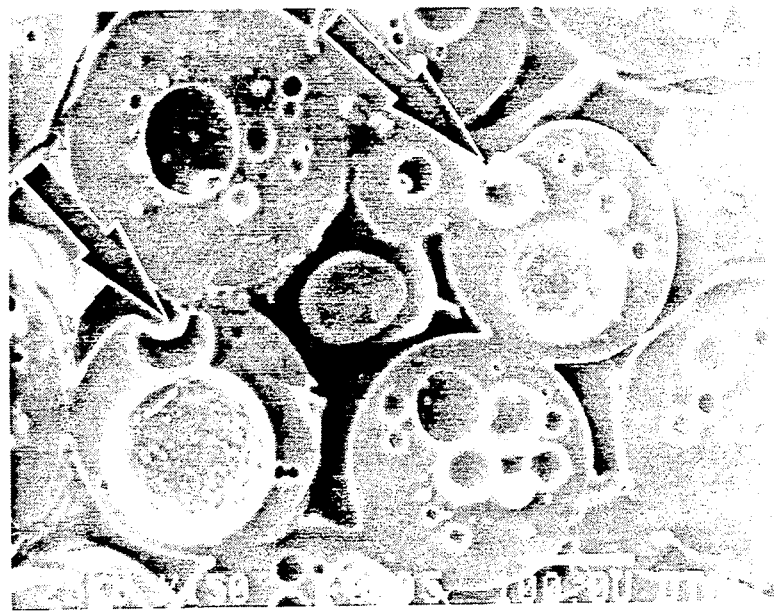
FIG. 7. Morphological changes of multi-phase PLGA microspheres containing brilliant blue during an in vitro dissolution test. The samples (initial (A)) were observed after a week (B), 2 weeks (C) and 4 weeks (D) by scanning electron microscopy.
Figure 7B:
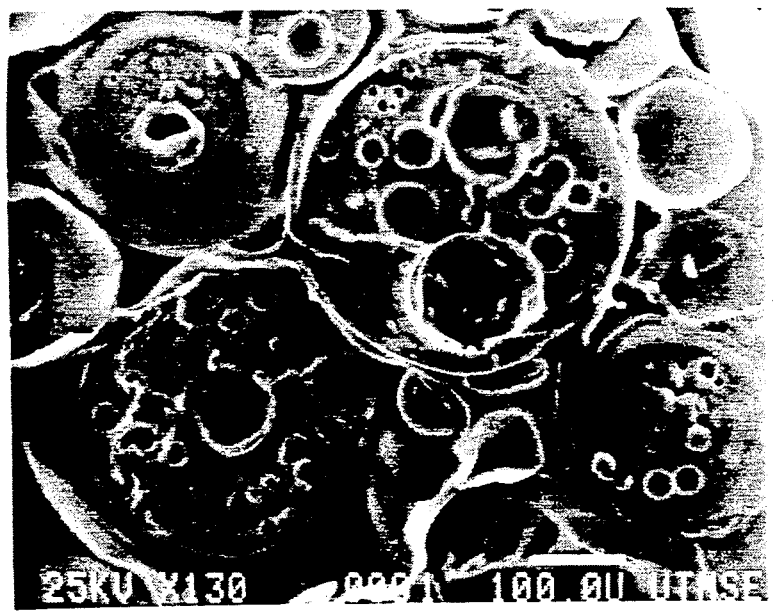
Figure 7C:
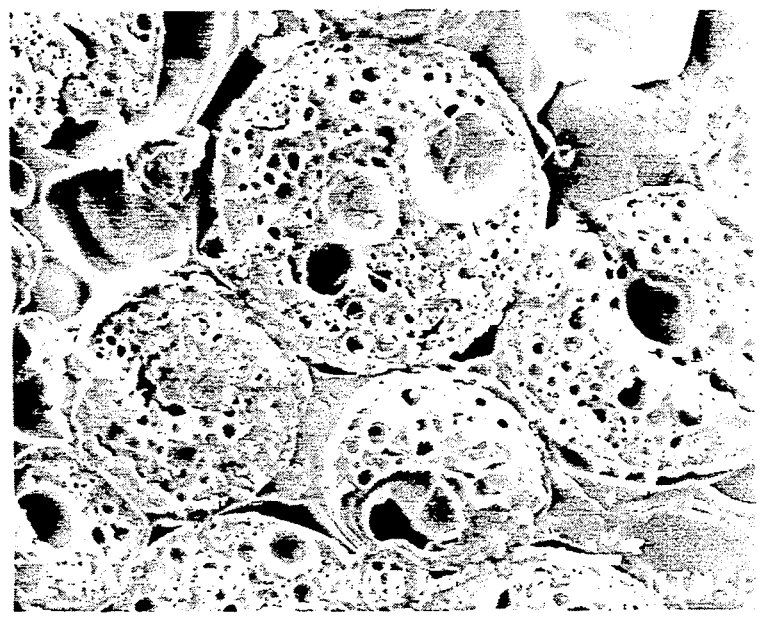
Figure 7D:

The outer surface and cross sections of the multi-phase PLGA microspheres containing brilliant blue were observed by SEM (FIG. 5-A and 5-B, respectively). The smaller "pock"-like depressions seen at the surface of some microspheres are postulated to have been created during the final solvent removal process (FIG. 5-B). When the multi-phase microspheres were placed under a high vacuum to remove residual solvent, the vaporization of residual acetonitrile and partial removal of water inside the microspheres caused the surface of the beads to expand in thin or weak areas beneath which the W/O emulsions existed (FIG. 5-B). The "stretched" areas were observed to result in depressions or irregularities in surface structure when the vacuum was removed.

Cavities found upon cross-sectioning the microspheres were the result of vacuum-induced evacuation of the W/O emulsion during the sample preparation process for SEM (FIG. 5-A). Some of the particles that remained in the cavities resulted from the aqueous phase of the W/O emulsion that had previously existed in the cavities.

Figure 15A:
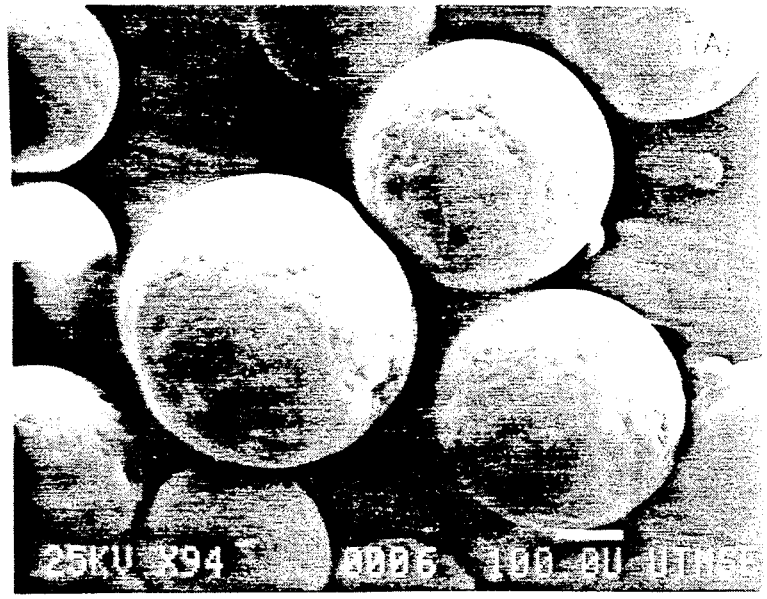
FIG. 15. Scanning electron micrographs of conventional PLGA microspheres containing brilliant blue prepared by a "W"/O emulsion solvent evaporation technique, showing entire particles (A) and cross-sections (B).
Figure 15B:
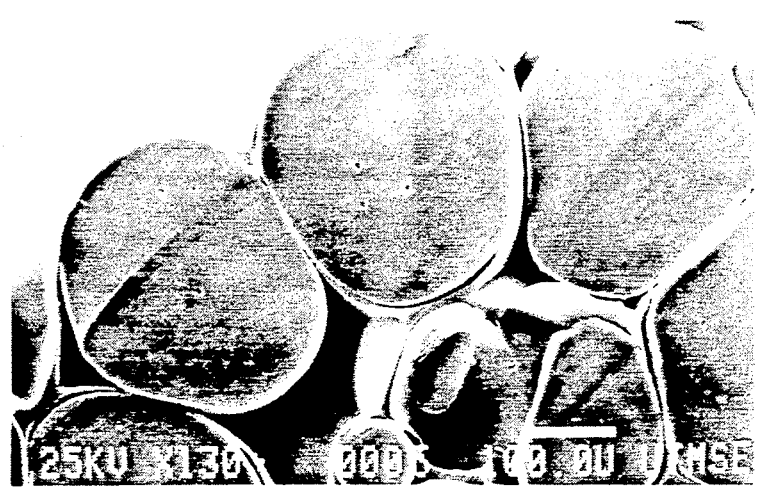

Conventional microspheres of PLGA containing brilliant blue dispersed in the polymer are shown in FIG. 15-A and 15-B. These microspheres did not have vacuolate structures in their cross sections (FIG. 15-B). The conventional microspheres demonstrated a less smooth, rough outer surface than the multi-phase microspheres (FIG. 15-A).

EXAMPLE 6

Comparison of Loading Efficiencies, Release Properties and Morphology of Conventional and Multi-phase PLGA Microspheres With CPM, DPH, PMZ, PRC and Brilliant Blue The present example is provided to demonstrate the superior drug loading efficiencies and slow-drug release characteristics of multi-phase microspheres compared to conventional microspheres. Morphological differences between multi-phase and the conventional microspheres is also described and demonstrated.

The multi-phase microspheres were prepared as described in Example 1. Conventional microspheres were prepared as described in Example 5. Each type of microsphere was prepared with one of each of the water-soluble molecular compounds brilliant blue CPM, DPH, PMZ, or PRC. However, it is expected that virtually the same results would manifest with any other water-soluble molecular compound, including biologically and pharmacologically potent peptides and proteins.

Morphological properties of the multi-phase PLGA microspheres during in vitro dissolution studies were compared to those of conventional PLGA microspheres which included the water-soluble molecular compound CPN, DPH, PMZ, PRC, or brilliant blue.

The multi-phase microspheres showed a slow drug release through cracks or failures on surface of the beads as the first stage and a rapid release stage as the second stage of dissolution. Porous sponge-like structures were seen in the polymer wall of both types of microspheres after 2 weeks although the outer surface of the beads remained almost intact after this time period. The water-soluble compound dissolution rate of the conventional microspheres increased as the drug content of the conventional microsphere increased. However the multi-phase microspheres demonstrated a dissolution rate which was independent of the drug content.

While the multi-phase microspheres demonstrated slower drug release properties that did the conventional microspheres, the polymer PLGA degradation rate of the multi-phase and the conventional microspheres were almost the same.

A. Determination of Drug Content in Microspheres

Water-soluble molecular compounds loaded into the conventional and multi-phase microspheres included brilliant blue, chlorpheniramine maleate (CPM), diphenhydramine hydrochloride (DPH), promazine hydrochloride (PMZ), and procainamide hydrochloride (PRC). The microspheres were first dissolved in methylene chloride. The brilliant blue remaining in the microspheres was extracted by distilled water. CPM was extracted from the microspheres with hydrochloric acid (0.01N) in similar fashion. The water-soluble drugs were extracted with the same procedure using dilute hydrochloric acid (0.01N HCl).

After sufficient agitation and partitioning time, the aqueous solutions containing the extracted drugs or dye were clarified by centrifugation at 2,000 rpm for 20 min. The drug content of each sample was evaluated by assay using uv-visible spectroscopy. The experimental drug loading efficiencies were calculated as a percentage of the theoretical drug content.

B. in Vitro Dissolution Studies

The multi-phase and the conventional microspheres (100–300 mg, 250–500 μm) were placed in 25 ml of pH 7.4, 0.01 M phosphate buffered saline (PBS) contained in a 30 ml test tube. The microspheres in the PBS were shaken using a rotating bottle apparatus (20 rpm) in a water bath at 37° C. Samples (5 ml) were withdrawn at appropriate time intervals using a glass syringe fitted with a nylon screen (50 μm) held in a polyethylene housing. After each withdrawal, the sample was replenished with 5 ml of PBS. Each sample was filtered using a 0.45 μm membrane filter. Absorbance of the samples were measured after appropriate dilutions.

1. Conventional Microspheres

Figure 9A:
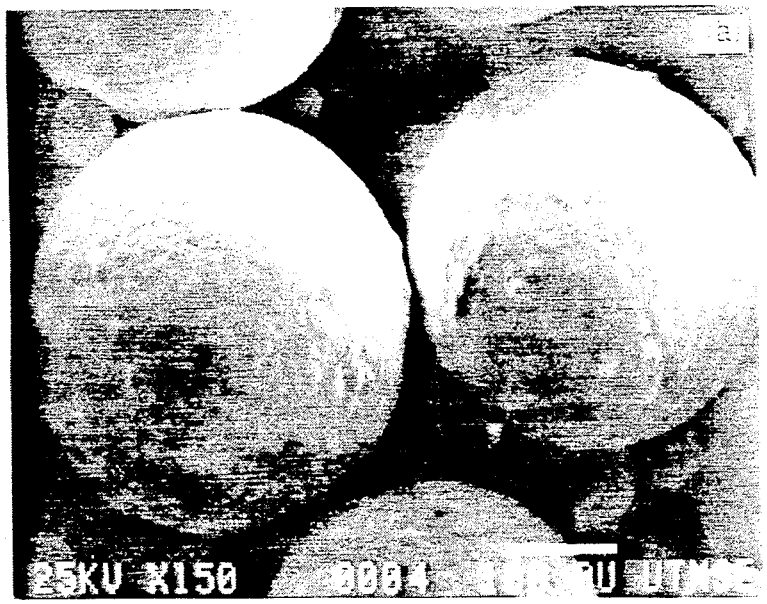
FIG. 9. Scanning electron micrographs of outward appearance of conventional (A) and multi-phase (B) microspheres observed after in vitro dissolution tests for 2 weeks.
Figure 9B:
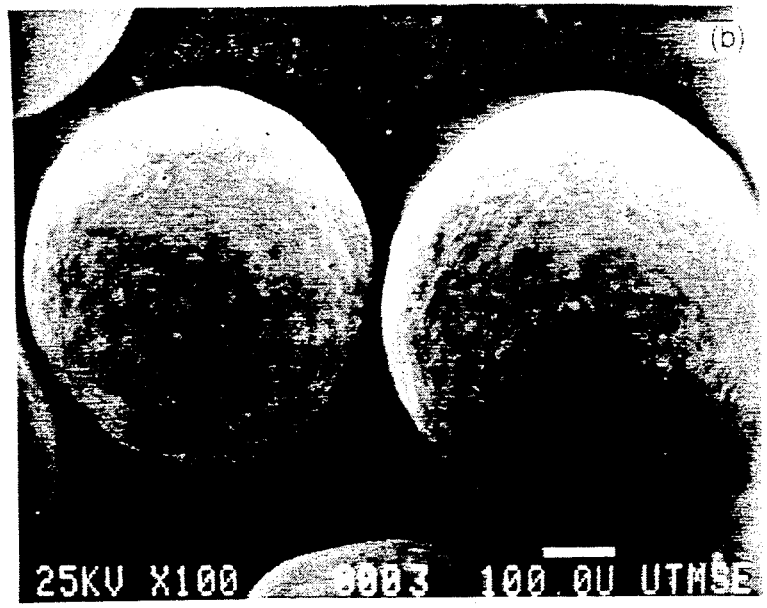

Lag time stages were observed in the release profiles of the conventional microspheres. This was attributed to the time required for water to penetrate into the polymer matrix and for sufficient polymer degradation to form aqueous channels through which the drug could diffuse out of the microspheres. During this lag time period, the erosion of the polymer wall of the conventional microspheres developed to form failures or cracks which were seen between the lamellas (FIG. 6-B). These lamellas were created by the polymer erosion along the discontinuous interfaces between the laminated PLGA precipitates which were hardened concentrically from the surface to the center of the beads. After 2 weeks, the porous sponge-like structures were observed in the polymer wall and the pores had developed toward the center of the beads. Some shallow portions beneath the surface of the beads had already eroded and evacuated. However, the surface portions of the beads remained almost intact even after 2 weeks (FIG. 9-A).

The second stage of the drug dissolution was thought to take place once aqueous channels had formed sufficiently for drug to diffuse out of the beads through the failures or the thin portions of the eroded surface.

The rate of drug release from conventional microspheres varied depending upon the drug content of the microsphere (see FIG. 3-A). In contrast, the rate of drug release from the multi-phase microspheres was relatively independent of the drug content of the microsphere (see FIG. 3-B).

2. Multi-Phase Microspheres

Slow dissolution (the first stage) of brilliant blue from the multi-phase microspheres was observed. This is hypothesized as being due to drug diffusion into the outer fluid from the W/O emulsion of the microspheres through thin portions of the polymer wall (see arrow in FIG. 5-A). Some of the thin areas of the microsphere surface had "dimples" which were observed on the multi-phase microspheres by SEM before the dissolution test (FIG. 5-B). These "dimples" were created during the final solvent removal process. When placed under a high vacuum, the microspheres were expanded in unhardened and thin areas of the surface. Once the vacuum was removed, the stretched surface portions resulted in the depressions or "dimples".

As the polymer wall swelled during the in vitro dissolution, highly drug permeable areas in the polymer walls of the multi-phase microspheres permitted the release of the drugs (see FIG. 7-A, thin walled portions at surface).

After two weeks, many pores had merged and formed porous sponge-like structures inside the beads (FIG. 7-B). These pores connected with each other, forming channels through which the water-soluble molecular compounds could diffuse (see FIG. 7-C and FIG. 7-D).

The internal surface on the inside of the cavities, in which the W/O emulsions once existed, did not appear eroded. The external surface of the multi-phase microspheres, in contacting with the mineral oil, also remained nearly intact as did the surface of the conventional microspheres.

A description of the morphological changes of the Conventional and the Multi-phase Microspheres during in vitro Dissolution Study follow in Section C.

C. Morphology of Microspheres and Polymer Degradation Scanning electron microscopy (SEN)—Morphological Analysis microspheres were coated with gold-palladium for 70 seconds under an argon atmosphere using a cold sputter module in a high-vacuum evaporator equipped with an omni-rotary stage. Samples were examined with a JOEL model 35 scanning electron microscope at 25 KV.

PLGA Molecular Weight Determination by Gel Permeation Chromatography (GPC)

Molecular weight of PLGA was determined by GPC in tetrahydrofuran using a set of three Ultrastyragel columns (Waters) with nominal pore size of $10^3$, $10^2$, and 10 nm, and a flow rate of 1 ml/min. The molecular weights were evaluated by elution volume against polystyrene standards (Polysciences, Inc.).

1. Conventional microspheres

Figure 4A:
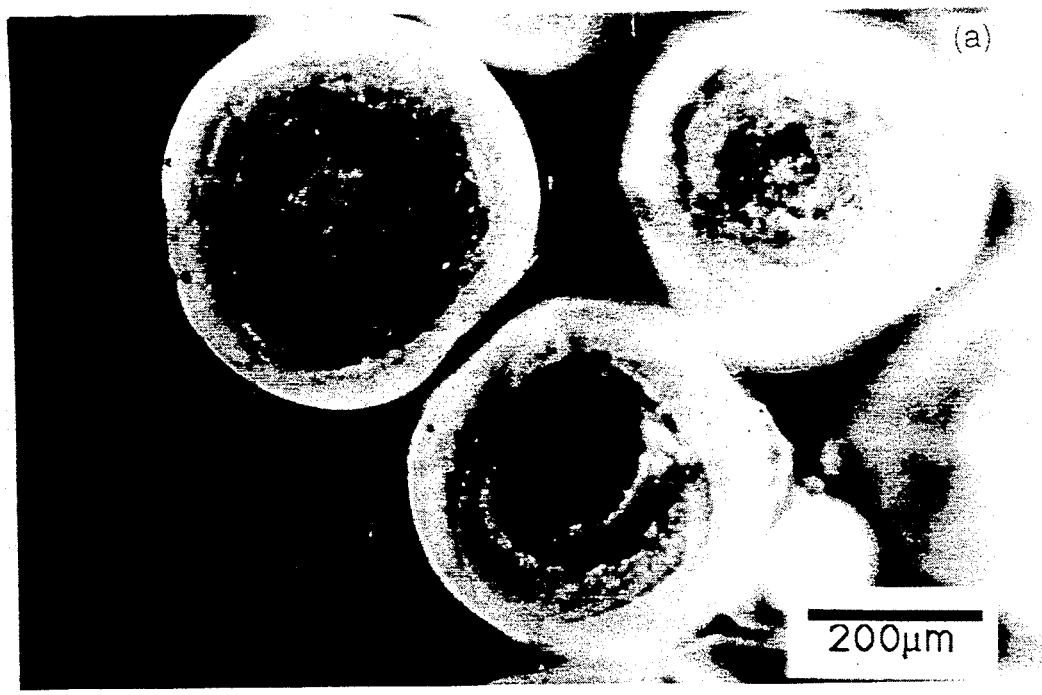
FIG. 4. Micrographs of a cross-section (A) and an outward appearance (B) of PLGA conventional microspheres containing brilliant blue after an in vitro dissolution test for a week.
Figure 4B:
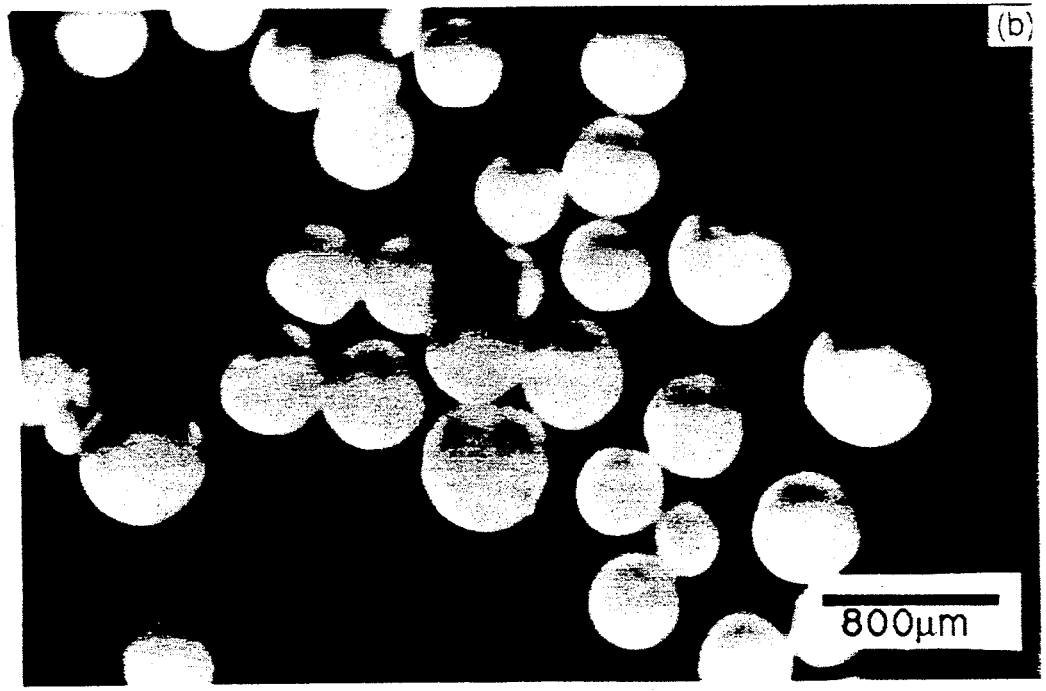

FIG. 4-A and 4-B show the cross-sections and the outward appearance, respectively, of the conventional microspheres containing brilliant blue (0.2 mg/g) which were observed after one week dissolution in vitro. The clear polymer walls of the microsphere beads turned white due to water uptake. Small pores, in which the brilliant blue particles had once existed, and concentric lamellar structures like onion peels were observed by SEM on the cross-section of the conventional microspheres (FIG. 4-A). These lamellar structures were not seen before the dissolution test. FIG. 6-C shows the cross sections of the microspheres observed after 2 weeks of the dissolution test. Erosion of the internal polymer wall had developed and porous sponge-like structures appeared. The inside of the microspheres were partially evacuated. However, the superficial portions of the beads remained almost intact. The rapid dissolution of the brilliant blue started around this stage. After 4 weeks, the porous structures of the internal polymer wall had mostly disappeared, but the polymer shells and residual masses still remained (FIG. 6-D).

2. Multi-Phase microspheres

FIG. 7-B shows a cross-section of the multi-phase microspheres containing brilliant blue (0.3 mg/g) observed by SEM after a week. The lamellar structures, which were seen on the cross-section of the conventional microspheres after a week, were not observed. The cross-sectional surfaces observed under reflected light appeared smooth and white due to the water uptake (FIG. 5-A). The brilliant blue dissolved gradually through cracks which were formed by erosion of the polymer on the surface at this stage. Dark spots of the penetrated brilliant blue diffused out of the W/O emulsions in the polymer beads, as seen on the surface of the microspheres.

FIG. 7-C shows a cross section of the multi-phase microspheres after 2 weeks of dissolution. Many pores appeared in the cross-sections of the polymer wall forming porous structures. The pores were larger than those of the conventional microspheres. Some of these pores became larger due to the erosion, and connected with each other to form aqueous channels through which drug could diffuse. However, the internal erosion of the polymer beads did not extend to the cavities which had contained the W/O emulsions.

After 4 weeks, when about 70% of the brilliant blue had been released, the superficial polymer walls and the porous structures of the microspheres remained (FIG. 7-D).

Molecular Weight Changes of PLGA of the Microspheres during the Release Test

Prior to the dissolution test and after 1, 2 and 4 weeks, the molecular weight of PLGA of the microspheres containing brilliant blue and CPM were determined by gel permeation chromatography (GPC) already described. FIG. 10 indicates the semi-log plots for -molecular weight changes of the residual solid PLGA of the conventional and the multi-phase microspheres containing brilliant blue (FIG. 10-A) and CPM (FIG. 10-B).

The PLGA polymer degradation rates of the conventional and multi-phase microspheres were virtually the same when the microspheres contained either brilliant blue or CPM. Thus, the inclusion of a water soluble compound and the particular amount of same in the W/O emulsion (microemulsion) in the multi-phase microspheres did not affect the PLGA degradation. In addition, the water soluble molecular compounds contained within the microspheres did not appear to affect the degradation of the polymer.

D. PLGA Degradation Properties During In Vitro Dissolution Test

The polymer walls which contacted with oil phase (soybean oil of the W/O emulsion in the microspheres and mineral oil used as the solvent evaporation medium for the preparation) seemed relatively stable compared to other portions of the polymer wall. However, the rates of the molecular weight reduction of PLGA in residual portion of each types of the microspheres were almost the same (see FIG. 10). Span 80, which was added to both the soybean oil and the mineral oil, may be adsorbed on the surface of the polymer beads causing protection from hydrolysis. In order to discuss the mechanism of the multi-phase microsphere erosion, further investigation of the polymer degradability and possible interactions with ingredients are needed.

The PLGA multi-phase microspheres demonstrated a two-stage release property which was independent of the brilliant blue and CPM content and their physiochemical characteristics, while the release profiles of the conventional matrix type microspheres had lag time and were affected by the drug content and the brilliant blue.

PROPHETIC EXAMPLE 7

Methods for Preparing Small Multi-phase Microspheres With Molecular Compound Therapeutic Agents The present prophetic example is provided to describe methods whereby the particle size of the microspheres may be reduced so as to provide a preparation of small (i.e., less than 150µ, preferably between about 50∞ to about 100µ) multi-phase microspheres. The present example will also outline methods whereby particular water soluble or partially water soluble proteins and peptides may be incorporated into the described multi-phase microsphere system.

Drugs such as decongestants, antihistamines, biological response modifiers (such as the interferons, interleukins, NAF (macrophage activating factor), SCF, TDF, EGF, EPO, TPA, ANP (arterial natriuretic peptide), etc.), antiviral agents (idoxuridine, amantadine, interferon, etc.), hemoproteins (P-450 enzymes, etc.), hormones (insulin, LHRH), enzymes (urokinase), may be prepared as part of a "microemulsion" in, for example, a volume of soybean oil, and then incorporated into the described multi-phase microsphere protocol outlined in Example 1 and FIG. 1.

The following particular modifications of that protocol will be required to facilitate the most efficacious preparation of multi-phase microspheres containing proteins and peptides: adjustment of the pH of the aqueous phase (which includes the particular water soluble drug) to the isoelectric point of the particular water soluble molecular compound. Stabilizing or protecting agent against degradation, denaturation, etc., may be necessary for the pharmacological activity of the protein, peptides and drug compounds.

A slight adjustment of the pH of the aqueous phase (i.e., the protein inside the oil droplet) and/or stabilizing agent for drugs may be necessary in order to enhance the stability of the protein (i.e., the microemulsion) and/or the solubility of the protein as part of the multi-phase microsphere preparation may be needed. Such may be accomplished by, for example, using the acid, hydrochloric acid, citric acid or sodium phosphate mono-basic to adjust the pH of the aqueous solution to the desired pH. Buffers such as phosphate buffer, acetate buffer and citrate buffer may also be used to adjust pH. By way of example, agents which may be used as stabilizing agents include sugars (glucose, sucrose, fructose, lactose, mannose, mannitol, etc) and polysaccharides (glycogen, starch, CMC-NA (sodium carboxymethycellulose), HPC (hydroxypropyl cellulose), HPMC (hydroxypropyl methyl cellulose), HPMCP (hydroxypropyl methyl cellulose phthalate), etc.), amino acids, peptides (albumin, globulin, gelatin, collagen, etc.), mucopolysaccharides (chondroitin sulfate, dextran sulfate, etc.), mucopolysaccharides (chondroitin sulfate, dextran sulfate, heparin sodium, hyaluronic acid, etc.), pluronic, polyethyleneglycols, polyacrylates, PVP (poly vinyl pyrollidone), and PVA (poly vinyl acetate).

A table of some exemplary water soluble and semi-water soluble proteins and peptides which could be used in conjunction with the multi-phase microspheres of the present invention appear in Table 4.

TABLE 4

Proposed Proteins and Peptides of Microsphere Systems

Protein/Peptide
Interferons (IFN-α,β,τ)
Macrophage Activating Factor (MAF)
Interleukins (IL-1,2,3,4,5,6)
6.8–7.3 (dominant) 5.3–5.8 (minor)
Colony Stimulating Factor (CSF)
Tumor Degenerating Factor (TDF)
Epidermal Growth Factor (EGF)
Erythropoietin (EPO)
Tissue Plasminogen Activator (TPA)
Insulin 5.3–5.35
Urokinase
Luteinizing Hormone Release Hormone (LHRH)
Monoclonal Antibodies
Superoxide Dismutase (SOD)
P-450
Bovine Serum Albumin (BSA)
Oxytocin Particular prophetic examples of specific water soluble compounds insulin, interleukin 1 and 2 follow.

Insulin Containing Multi-phase Microspheres

It may be necessary to adjust the pH of the aqueous phase contained in the W/O emulsion to the isoelectric point of insulin, which is between 5.3 to 5.35 (see Merck, 11th ed., p 4888) in order to accomplish the desired stability and/or solubility of the protein.

The microemulsion so adjusted for pH to solubilize/stabilize the protein, will then be mixed with a polymer containing solvent, such as PLA in acetonitrile, and the multi-phase microspheres prepared substantially as described for the remainder of the procedure in FIG. 1.

Interleukin Containing Multi-phase Microspheres

Multi-phase microspheres may be prepared with the particular family of proteins known as the interleukins, which include IL-1, 2, 3, 4, and 6. It may be necessary to adjust the pH of the aqueous phase contained in the W/O emulsion to the isoelectric point of the particular interleukin species. For example, the isoelectric point of the dominant species of interleukin 1 is between 6.8 to 7.3. The isoelectric point of the minor species of interleukin 1 is between 5.3 and 5.8. (see, the Merck Index, 11th Edition, p. 4895–4896). By adjustment of the W/O microemulsion or oily suspension of the interleukin, one may accomplish the desired stability and/or solubility of this particular agent in the system.

The aqueous suspension of the interleukin protein so adjusted for pH to enhance solubilization/stability of the protein, will then be mixed with a polymer containing solvent such as PLA acetonitrile. The multi-phase microspheres may then be prepared substantially as described for the remainder of the procedure outlined in FIG. 1.

Proposed Methods for Reducing Multi-phase Microsphere Size to Between 50μ–100μ

The multi-phase microspheres prepared thus far have a size of about 150μ. Microspheres of smaller diameter may be prepared by increasing the temperature of the oil phase, provided the drug is stable in the emulsion. Higher agitation speeds will also be successful if that is coupled with a high concentration of polymer in the acetonitrile to prevent the loss of emulsion from the microsphere. In addition, a dry (lyophilized) emulsion system can be used for preparation of multi-phase microspheres instead of the W/O microemulsion. Where a stainless steel propeller device is employed to agitate the multiple emulsion, agitation speeds should be increased to, for example, 250, 400, 500 and 600 rpm to achieve small (<150μ) multi-phase microspheres.

While those of skill in the pharmaceutical and/or polymeric drug delivery chemical arts will be able to practice the present invention with the aid of the disclosure provided here, the following references may facilitate practice or enhanced understanding of certain aspects. Inclusion of a reference in this list is not intended to and does not constitute an admission that the reference constitutes prior art with respect to the present invention. The following references are specifically incorporated herein in pertinent part by reference.

1. Bodmeier, R. and McGinity, J. W. (1987), Pharmaceutical Research, 4:465.
2. Bodneier, R. and McGinity, J. W. (1988), J. Microencapsulation, 5:325.
3. Jalil, R. and Nixon, J. R. (1990), J. Microencapsulation, 7:229.
4. Jalil, R., and Nixon, J. R. (1990), J. Microencapsulation, 7:53.
5. Csernus, V. J. et al. (1990), Int. J. Peptide Protein Res., 35:557.
6. Okada, H. et al. (1988), J. Pharmacol. Exp. Ther., 244:744.
7. Johnson, R. E. et al. (1990), Pharmaceutical Res., 7(9):S181.
8. Tsai, D. C. et al. (1986), J. Microencapsulation, 3:181.
9. Merck Index, 11th Edition, (1983), Windholz et al., editors, Merck & Co., Inc., Publishers, pp.4888, 4895, 4896.
10. Gilding, D. K., et al. (1979), Polymer, 20:1459.
11. Leelarasamee, N. et al. (1986), J. Microencapsulation, 3:171-179.
12. Juni, K. et al. (1985), Chem. Pharm. Bull., 33(1):313-318.
13. Cavalier, M., et al. (1986), J. Pharm. Pharmacol., 38:249-253.
14. Spenlehauer, G., et al. (1986), J. Pharm. Sci., 75(8):750-755.
15. Bodmeier, R. and McGinity, J. W. (1988), Int. J. Pharm., 43:179-186.
16. Lin, S. Y., et al. (1986), Biomat., Med. Devices and Arti. Organs, 13(3,4):187-201.
17. Sanders, L. M., et al. (1985), J. Contr. Rel., 2:187-195.
18. Jalil, R. and Nixon, J. R. (1989), J. Microencapsulation, 6(4):473-484.
19. Jalil, R. and Nixon, J. R. (1990a), J. Microencapsulation, 7(1):25-39.
20. Jalil, R. and Nixon, J. R. (1990b), J. Microencapsulation, 7(1):41-52.
21. Cohen et al. (1991), Pharm. Res., 9:713-719.
22. Morris, N. J. and Warburton, B. (1982), J. Pharm. Pharmacol., 34:475-479.
23. Saha, M. V. et al. (1987), J. Microencapsulation, 4(3):223-238.
24. U.S. Pat. No. 4,711,782—Okada et al. (1987)
25. U.S. Pat. No. 4,728,721—Yamamoto et al. (1988)
26. U.S. Pat. No. 4,954,298—Yamamoto et al. (1990)
27. Hora et al. (1990), Pharmaceutical Research, 7(11):1190-94.
28. U.S. Pat. No. 4.273,920—Nevin (1981)
29. McGraw-Hill Dictionary of Scientific Terms, 3rd edition (1984) McGraw-Hill Publishers, p. 540.
30. Modern Chemistry, 3d. Edition (1990), Hold, Rinehard and Winston, Inc. Publishers. pp. 414-415.
31. Bodmeier, R., and McGinity, J. W. (1988), J. Microensapsulation, 4:279.
32. Makino, K., Ohshima, H., and Kondo, T. (1987) Pharmaceutical Research, 4:62.
33. Williams, D. F., and Mort, E. (1977), J. Bioengineering, 1:231.
34. Asano, M., et al (1989), J. Controlled Release, 9:111.

What is claimed is:

1. A delivery system for a protein, peptide, or drug with biodegradable multi-phase microspheres, said microspheres comprising a protein, peptide, or drug contained within a fixed oil and an essentially water insoluble, biodegradable polymeric matrix comprised of polylactic acid or polylactic glycolic acid wherein the polymeric matrix surrounds the fixed oil of the microsphere and wherein the fixed oil contains the protein, peptide, or drug.

2. A delivery system for a water-soluble protein, peptide, or drug with biodegradable multi-phase microspheres, said microspheres comprising a microemulsion of a water soluble protein, peptide, or drug, a fixed oil and a biodegradable, essentially water insoluble polymeric matrix of polylactic acid or polylactic glycolic acid, said polymeric matrix surrounding the microemulsion of fixed oil and the protein, peptide, or molecular compound.

3. A delivery system for cytokines with biodegradable multi-phase microspheres, said microspheres comprising a cytokine contained within a fixed oil, and an essentially water insoluble, biodegradable polymeric matrix of polylactic acid or polylactic glycolic acid, wherein the polymeric matrix surrounds the fixed oil and wherein the fixed oil contains the cytokine.

4. A delivery system for tumor necrosis factor with biodegradable multi-phase microspheres said microspheres comprising a lyophilized microemulsion of an aqueous solution of tumor necrosis factor in a fixed oil, and an essentially water insoluble, biodegradable polymeric matrix of polylactic acid or polylactic glycolic acid, wherein the polymeric matrix surrounds said microemulsion of tumor necrosis factor and fixed oil.

5. The delivery system of claim 1 wherein the molecular compound is a protein, a peptide, a chemical or a dug.

6. The delivery system of claim 1, 2, 3 or 4 wherein the multi-phase microsphere is about 150μ in size.

7. The delivery system of claim 1, 2, 3 or 4 wherein the multi-phase microsphere is about between 50μ to 100μ in size.

8. The delivery system of claim 1 wherein the molecular compound is water soluble and pharmacologically active.

9. The delivery system of claim 8 wherein the molecular compound is prepared as an aqueous solution together in a fixed oil to provide a microemulsion.

10. The delivery system of claim 1 wherein the molecular compound is an enzyme.

11. The delivery system of claim 1 wherein the molecular compound is selected from the group consisting of interferon, macrophage activation factor, interleukin, colony stimulating factor, tumor degenerating factor, epidermal growth factor, erythropoietin, tissue plasminogen activator, insulin, urokinase, luteinizing hormone releasing hormone, superoxide dismutase, or an antibody or an enzyme.

12. The delivery system of claim 1 wherein the molecular compound is chlorpheniramine maleate, diphenhydramine hydrochloride, procainamide hydrochloride, promazine hydrochloride, or brilliant blue.

13. The delivery system of claim 1, 2, 3 or 4 wherein the multi-phase microspheres are comprised of a biodegradable polymer of lactic acid or glycolic acid.

14. The delivery system of claim 1, 2, 3 or 4 wherein the microspheres are comprised of a polymer poly (d,l)-lactic, poly (l)-lactic acid, or copolymers of lactic and glycolic acid.

15. The delivery system of claim 1, 2, 3 or 4 wherein the fixed oil is safflower, soybean, cottonseed, peanut, sesame or cod liver oil.

16. The delivery system of claim 1 wherein the molecular compound is tumor necrosis factor.

17. The delivery system of claim 4 or 6 wherein the microemulsion consists of lyophilized tumor necrosis factor in a fixed oil and the polymeric matrix is poly-lactic acid (PLGA).

18. The delivery system of claim 17 wherein the fixed oil is soybean oil and includes aluminum monostearate.

19. A method for providing sustained release of a protein, peptide, or drug in an animal comprising:
preparing a formulation of microspheres, said microspheres containing the protein, peptide, or drug in a fixed oil, and a biodegradable essentially water insoluble polymeric matrix of polylactic acid or polylactic glycolic acid; and
administering an amount of the formulation effective to provide sustained release of the protein, peptide, or drug in the animal for a prescribed period of time, wherein the polymeric matrix surrounds the fixed oil and the fixed oil contains the protein, peptide, or drug.

20. The method of claim 19 wherein the water-soluble molecular compound is a protein, a peptide, a chemical, or a drug.

21. The method of claim 19 wherein the molecular compound is a therapeutic agent.

22. The method of claim 19 wherein the molecular compound is CPM, DPH, PMZ, TNF or PRC.

23. The method of claim 19 wherein the formulation is administered parenterally.

24. The method of claim 19 wherein the formulation is administered intramuscularly.

25. The method of claim 19 wherein the protein, peptide, or drug is water-soluble and is prepared as an aqueous solution together in a fixed oil to provide a microemulsion and wherein the polymeric matrix surrounds the microemulsion.

26. The method of claim 19 wherein sustained release of the molecular compound is provided for up to 1 year.

27. The method of claim 19 wherein sustained release of the molecular compound is provided for about 3 months.

28. The method of claim 19 wherein the molecular compound is water-soluble.

29. A method for preparing multi-phase microspheres containing a protein, peptide, or dug comprising:
mixing an aqueous solution of the protein, peptide, or drug with a fixed oil to form a W/O microemulsion;
mixing polylactic acid or polylactic glycolic acid and a polymer solvent together to form a polymer solution;
dispersing the microemulsion into the polymer solution to form a W/O/"O" emulsion;
mixing the W/O/"O" emulsion together in a dispersion oil which is incompatible with the polymer solvent to form a multiple emulsion;
agitating and removing the solvent from the multiple emulsion to form hardened microspheres; and
washing and drying the hardened microspheres to form multi-phase microspheres containing the water-soluble protein, peptide, or drug.

30. The method of claim 29 wherein the fixed oil of the microemulsion is soybean, cottonseed, peanut, sesame cod liver oil or safflower oil.

31. The method of claim 29 wherein the polymer solvent is acetonitrile or methylene chloride.

32. The method of claim 29 wherein the polymer is PLA or PLGA.

33. The method of claim 29 wherein the polymer solution comprises PLA and acetonitrile.

34. The method of claim 29 wherein the molecular compound is a protein, a peptide, a chemical or a drug.

35. The method of claim 29 wherein the microspheres are about 150μ in size.

36. The method of claim 29 wherein the microspheres are between about 50μ and about 100μ in size.

37. The method of claim 29 wherein the molecular compound is water soluble and is selected from the group consisting of CPM, DPH, brilliant blue, PMZ, and PRC.

38. The method of claim 29 wherein the microemulsion comprises about 1% w/w Tween 80 of the microemulsion.

39. The method of claim 29 wherein the microemulsion comprises about 2% aluminum monostearate and about 5% W/W Span 80 of the microemulsion.

40. The method of claim 29 wherein the multiple emulsion comprises about 0.25% to 2% w/w Span 80.

41. The method of claim 29 wherein the molecular compound is:
insulin;
LHRH;
a steroid;
atriopeptin III;
monoclonal antibodies;
TNF;
interferon;
macrophage activating factor;
interleukins;

colony stimulating factor;
tumor degenerating factor;
epidermal growth factor;
erythroprotein;
tissue plasminogen activator;
urokinase;
superoxide dismutase or
P-450.

42. The method of claim 2 wherein the ratio of microemulsion to polymer is between about 0.25 to 1.0 grams to 1 by weight.

43. The method of claim 29 wherein the molecular compound is unstable in water, and wherein the microemulsion is lyophilized prior to dispersing the microemulsion into the polymer solution to form a W/O/"W" emulsion.

44. The method of claim 43 wherein the molecular compound is TNF.

45. A method for preparing microspheres containing a water-soluble drug comprising:
preparing a first mixture of a water-soluble drug in water, gelatin and Tween 80 to form an aqueous phase;
preparing a second mixture of an amount of aluminum stearate and a volume of a fixed oil to produce a 2% w/w aluminum stearate and about 5% w/w Span 80 oil phase;
combining the first mixture with the second mixture to form a coarse W/O emulsion;
processing the coarse W/O emulsion into a fine W/O microemulsion;
preparing a third mixture of polylactic acid or polylactic glycolic acid and a solvent;
combining a quantity of the fine W/O microemulsion with the third mixture to form a W/O/"O" emulsion;
preparing a fourth mixture of an amount of Span 80 and an oil incompatible with the polymer solvent;
pouring the W/O/"O" emulsion into the fourth mixture to form a multiple emulsion;
agitating and evaporating the polymer solvent from the multiple emulsion to form hardened microspheres;
separating the hardened microspheres from the mixture; and
washing and drying the hardened microspheres to form multi-phase microspheres containing a water-soluble drug.

46. The method of claim 45 wherein the third mixture comprises less than 35% w/w of the polymer.

47. The method of claim 45 wherein the third mixture comprises about 33% w/w of a PLA biodegradable polymer in an acetonitrile solvent.

48. The method of claim 45 wherein the third mixture comprises about 31% w/w of a PLGA biodegradable polymer in an acetonitrile solvent.

49. The method of claim 45 wherein the water-soluble molecular compound is CPM, DPH, PMZ, or PRC.

50. The method of claim 45 wherein the quantity of the fine W/O emulsion is between about 0.25 to 1.0 g by weight of the W/O/"W" emulsion.

51. The method of claim 45 wherein the fourth mixture includes between about 0.25% to about 2% w/w Span 80.

52. The method of claim 45 wherein the fourth mixture includes about 0.254 to 0.5% w/w Span 80.

53. The method of claim 45 wherein the fourth mixture includes about 0.254 w/w Span 80.

54. A multi-phase microsphere for the delivery of a peptide, protein, or drug comprising a biodegradable essentially water insoluble polymeric matrix of polylactic acid or polylactic glycolic acid surrounding a protein, peptide, or drug contained within a fixed oil, said microsphere prepared by a process of:
preparing a first mixture of a water-soluble protein, peptide, or dug in water, gelatin and Tween 80 to form an aqueous base;
preparing a second mixture of an amount of aluminum stearate and a volume of a fixed oil to produce a 2% w/w aluminum stearate and about 5% w/w span 80 oil phase;
combining the first mixture with the second mixture to form a coarse W/O emulsion;
processing the coarse W/O emulsion into a fine W/O micro emulsion;
preparing a third mixture of a biodegradable essentially water-insoluble polymer polylactic acid of polylactic glycolic acid and a solvent;
combining a quantity of the fine W/O micro emulsion with the third mixture to form a W/O/"O" emulsion;
preparing a fourth mixture of an amount of span 80 and an oil incompatible with the polymer solvent;
pouring the W/O/"O" emulsion into the fourth mixture to form a multiple emulsion;
evaporating the solvent from the multiple emulsion to form hardened microspheres;
separating the hardened microspheres from the mixture; and
washing and drying the hardened microspheres to form multi-phase microspheres containing a water-soluble protein, peptide, or drug.

55. The microsphere of claim 54 wherein the fixed oil is safflower, soybean, cottonseed, peanut, sesame or cod liver oil.

56. The microsphere of claim 54 wherein the protein is tumor necrosis factor.

57. The microsphere of claim 54 wherein the biodegradable polymer is poly(d,l-lactic acid) or poly(d,l-lactic) co-glycolic lactic acid.

58. A biodegradable polymeric microsphere comprising an essentially water insoluble poly (d,l-lactic acid) or poly (d,l-lactic) co-glycolic acid polymeric matrix surrounding a protein-containing fixed oil droplet.

59. The biodegradable polymeric microsphere of claim 58 wherein the polymeric matrix is poly(d,l-lactic acid).

60. The biodegradable polymeric microsphere of claim 58 wherein the fixed oil is safflower, soybean, cottonseed, peanut, sesame or cod liver oil.

61. The biodegradable polymeric microsphere of claim 58 wherein the protein is tumor necrosis factor of interleukin-1.

62. The biodegradable polymeric microsphere of claim 58 wherein the microsphere has a diameter of between $50\mu$ and $200\mu$.

* * * * *

UNITED STATES PATENT AND TRADEMARK OFFICE
CERTIFICATE OF CORRECTION

PATENT NO. : 5,288,502

DATED : February 22, 1994

INVENTOR(S) : James W. McGinity and Motokazu Iwata

It is certified that error appears in the above-identified patent and that said Letters Patent is hereby corrected as shown below:

In claim 5, column 30, line 68, delete the word "dug" and insert therefore --drug--.

In claim 29, column 32, line 14, delete the word "dug" and insert therefore --drug--.

In claim 30, column 32, line 33, after the word "sesame" insert therefore --,--.

In claim 39, column 32, line 55, delete "W/W" and insert therefore --w/w--.

In claim 42, column 33, line 10, delete "2" and insert therefore --29--.

In claim 52, column 34, line 5, delete "0.254" and insert --025%--

In claim 53, column 34, line 7, delete "0.254" and insert --0.25%--

Signed and Sealed this

Thirtieth Day of August, 1994

Attest:

BRUCE LEHMAN

Attesting Officer     Commissioner of Patents and Trademarks